United States Patent
Belknap et al.

(10) Patent No.: US 10,961,541 B2
(45) Date of Patent: Mar. 30, 2021

(54) GENETICALLY ALTERED GUAYULE HAVING INCREASED RUBBER PRODUCTION AND METHODS THEREOF

(71) Applicant: The United States of America, as represented by the Secretary of Agriculture, Washington, DC (US)

(72) Inventors: William R. Belknap, Eugene, OR (US); Colleen M. McMahan, Sausalito, CA (US); Jose A. Valdes Franco, Ithaca, NY (US); Yong Q. Gu, Richmond, CA (US); Grisel P. Ponciano, Castro Valley, CA (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/126,124

(22) Filed: Sep. 10, 2018

(65) Prior Publication Data

US 2019/0085343 A1 Mar. 21, 2019

Related U.S. Application Data

(60) Provisional application No. 62/560,323, filed on Sep. 19, 2017.

(51) Int. Cl.
| | |
|---|---|
| *C12N 15/82* | (2006.01) |
| *C07K 14/415* | (2006.01) |
| *C12N 15/70* | (2006.01) |
| *C12N 15/80* | (2006.01) |

(52) U.S. Cl.
CPC ........ *C12N 15/8201* (2013.01); *C07K 14/415* (2013.01); *C12N 15/8223* (2013.01); *C12N 15/8237* (2013.01); *C12N 15/8243* (2013.01); *C12N 15/70* (2013.01); *C12N 15/80* (2013.01)

(58) Field of Classification Search
None
See application file for complete search history.

(56) References Cited

U.S. PATENT DOCUMENTS

| | | | |
|---|---|---|---|
| 5,633,433 | A | 5/1997 | Backhaus et al. |
| 6,132,711 | A | 10/2000 | Backhaus et al. |
| 6,541,682 | B1 | 4/2003 | Nehra et al. |
| 7,129,392 | B2 | 10/2006 | Hahn et al. |
| 9,018,449 | B2 | 4/2015 | Dong et al. |
| 9,523,097 | B2 | 12/2016 | Kang et al. |
| 9,574,203 | B1 | 2/2017 | Dong et al. |
| 2003/0150008 | A1 | 8/2003 | Karunanandaa et al. |
| 2006/0217512 | A1 | 9/2006 | Mau et al. |
| 2006/0218660 | A1 | 9/2006 | Dong et al. |
| 2014/0325699 | A1 | 10/2014 | Kang et al. |
| 2018/0127767 | A1 | 5/2018 | Scheller et al. |

FOREIGN PATENT DOCUMENTS

EP 0675202 A1 3/1994

OTHER PUBLICATIONS

Definition "Germplasm" (2020) downloaded from https://www.thefreedictionary.com/germplasm on Jan. 21, 2020. Pasted into the body of the rejection. (Year: 2020).*
Stonebloom et al. Transcriptome analysis of rubber biosynthesis in guayule (*Parthenium argentatum* gray). (2019) BMC Plant Biology; vol. 19; pp. 1-10 (Year: 2019).*
Akhtar et al. The tomato cis-prenyltransferase gene family. (2013) The Plant Journal; vol. 73; pp. 640-652 (Year: 2013).*
Whalen et al. PBC060H05_08145 Parthenium argentatum cold acclimated bark cDNA library (PBC) Parthenium argentatum cDNA clone PBC060H05, mRNA sequence. (2010) GenBank Accession GW783717.1; pp. 1-2 (Year: 2010).*
Cornish et al. The potential for sunflower as a rubber-producing crop for the United States. (2007) Helia; vol. 30; pp. 157-166 (Year: 2007).*
Whalen et al. "Development of Crops to Produce Industrially Useful Natural Rubber" (2013) Chapter 23 in Isoprenoid Synthesis in Plants and Microorganisms; eds.: Bach and Rohmer, Springer-Verlag, New York; pp. 329-345 (Year: 2013).*
Langlade et al. Putative undecaprenyl pyrophosphate synthetase family protein [*Helianthus annuus*]. (2017) Gen Bank Accession OTG12218.1; p. one of one (Year: 2017).*
Jiang et al. Molecular switch for cold acclimation—anatomy of the cold-inducible promoter in plants. (Biochemistry (Moscow) (2013) vol. 78; pp. 451-465 (Year: 2013).*
Archer, Bernard L. et al. "New Aspects of Rubber Biosynthesis," Botanical Journal of the Linnean Society, (1987), 94:181-196 with 6 figures.
Backhaus, Ralph A. et al., "Purification and Characterization of an Abundant Rubber Particle Protein From Guayule," Phytochemistry, (1991), 30(8):2493-2497.
Cornish, Katrina et al., "Effect of Different Allylic Diphosphates on the Initiation of New Rubber Molecules and on Cis-1,4-polyisoprene. Biosynthesis in Guayule (*Parthenium argentatum* Gray)," (1995), J. Plant Physiol., 147:301-305.
Da Costa, Bernardo M.T. et al., "Magnesium ion regulation of in vitro rubber biosynthesis by Parthenium argentatum Gray," Phytochemistry, (2006); 67:1621-1628.
Da Luna, Phil et al., "A Molecular Dynamics Examination on Mutation-Induced Catalase Activity in Coral Allene Oxide Synthase," (2013), The Journal of Physical Chemistry, 117:14635-14641.
Gao, Benlian et al., "Role of the conserved distal heme asparagine of coral allene oxide synthase (Asn137) and human catalase (Asn148): mutations affect the rate but not the essential chemistry of the enzymatic transformations," NIH Public Access Author Manuscript Arch Biochem Biophys, (2008), 477(2):285-290.

(Continued)

*Primary Examiner* — Cathy Kingdon Worley
(74) *Attorney, Agent, or Firm* — John D. Fado; Ariel L. Atkinson

(57) ABSTRACT

Genetically altered guayule are generated which produce more rubber than the amount of rubber produced by a wild-type guayule. The genetically altered guayule plant contains an expression vector that encodes a protein involved in rubber production. Method of making and using the genetically altered guayule are included.

26 Claims, 7 Drawing Sheets
Specification includes a Sequence Listing.

(56) References Cited

OTHER PUBLICATIONS

Guo, Weiwen et al., "Characterization of a Cold-Regulated Wheat Gene Related to *Arabidopsis* cor47'," Plant Physiol., (1992), 100:915-922.

Harms, Karsten et al., "Expression of a Flax Allene Oxide Synthase cDNA Leads to Increased Endogenous Jasmonic Acid (JA) Levels in Transgenic Potato Plants but Not to a Corresponding Activation of JA-Responding Genes," The Plant Cell, (1995), 7:1645-1654.

Keller, Beat et al., "Vascular-Specific Expression of the Bean GRP 1.8 Gene 1s Negatively Regulated," The Plant Cell, (1991); 3:1051-1061.

Kim, Chi-Yeol et al., "Functional analysis of a cold-responsive rice WRKY gene, OsWRKY71," Plant Biotechnol Rep, Plant Biotechnol Rep, pp. 1-11.

Kim, In Jeong et al., "A novel cDNA from Parthenium argentatum Gray enhances the rubber biosynthetic activity in vitro*," Journal of Experimental Botany, (2004), 55(396):377-385.

Rojruthai, Porntip et al., "In vitro synthesis of high molecular weight rubber by Hevea small rubber particles," Journal of Bioscience and Bioengineering, (2010),109(2):107-114.

Sakdapipanich, Jitladda Tangpakdee et al., "Structural Characterisation of the Small Rubber Particles in Fresh Hevea Latex," J. Rubb. Res., (1999), 2(2):160-165 and 2(3):166-168.

Sansatsadeekul, Jitlada et al., "Characterization of associated proteins and phospholipids in natural rubber latex," Journal of Biosciences and Bioengineering, (2011), 111(6):628-634.

Sauer, Norbert et al., "SUC1 and SUC2: two sucrose transporters from *Arabidopsis thaliana*; expression and characterization in baker's yeast and identification of the histidinetagged protein," The Plant Journal, (1994), 6(1):67-77.

Hirschey, Matthew D. et al., "Sirtuins: Methods and Protocols," Methods in Molecular Biology, (2013), vol. 1077, pp. 1-311.

Tosha, Takehiko et al., "On the Relationship of Coral Allene Oxide Synthase to Catalase, A Single Active Site Mutation That Induces Catalase Activity in Coral Allene Oxide Synthase," The Journal of Biological chemistry, (2006), 281(18): 12610-12617.

Van Beilen, Jan B., et al., "Establishment of new crops for the production of natural rubber," Trends in Biotechnology, 25(11):522-529.

Van Beilen, Jan B., et al., Guayule and Russian Dandelion as Alternative Sources of Natural Rubber, Critical Reviews in Biotechnology, (2007), 27(4):217-231.

Wang, Cunxi et al., "Overexpression of a cytoplasm-localized allene oxide synthase promotes the wound-induced accumulation of jasmonic acid in transgenic tobacco," Plant Molecular Biology, (1999), 40:783-793.

Yamashita, Satoshi et al., "Identification and reconstitution of the rubber biosynthetic machinery on rubber particles from Hevea brasiliensis," eLife, (2016), pp. 1-28.

Zarka, Daniel G. et al., "Cold Induction of *Arabidopsis* CBF Genes Involves Multiple Ice (Inducer of CBF Expression) Promoter Elements and a Cold-Regulatory Circuit That Is Desensitized by Low Temperature," Plant Physiol., (2003), 133:910-918.

Lakusta, Adam M. et al., "Characterization of cis-prenyltransferase complexes in guayule (*Parthenium argentatum*), an alternative natural rubber-producing plant," Paper by Lakusta et al., (2018), pp. 1-32.

Li, Meng et al., "Strength comparison between cold-inducible promoters of *Arabidopsis* cor15a and cor15b genes in potato and tobacco," Plant Physiology and Biochemistry, (2013), 71:77-86.

Macrae, Sharmane et al., "Rubber Production in Guayule: Determination of Rubber Producing Potential," Plant Physiol., (1986), 81:1027-1032.

Medina, Joaquin et al., "Developmental and Stress Regulation of RCI2A and RCI2B, Two Cold-Inducible Genes of *Arabidopsis* Encoding Highly Conserved Hydrophobic Proteins1," Plant Physiologist, (2001), 125:1655-1666.

Miyata, Luzia Yuriko et al., "GUS expression in sweet oranges (*Citrus sinensis* L. Osbeck) driven by three different phloem-specific promoters," Plant Cell Rep, (2012); 31(11):2005-2013.

Mooibroek, H. et al., "Alternative sources of natural rubber," Appl Microiol Biotechnol, (2000), 53:355-365.

Nawamawat, Kanjanee et al., "Surface nanostructure of Hevea brasiliensis natural rubber latex particles," Colloids and Surfaces A: Physicochemical and Engineering Aspects,(2011), 390:157-166.

Oldham, Michael L., et al., "The structure of coral allene oxide synthase reveals a catalase adapted for metabolism of a fatty acid hydroperoxide," PNAS, (2005), 102(2):297-302.

Ouellet, Francis et al., "The wheat wcs120 promoter is cold-inducible in both monocotyledonous and dicotyledonous species," FEBS Letters, (1998), 423:324-328.

Ohya, Norismasa et al., "Activity of Rubber Transferase and Rubber Particle Size in Hevea Latex," J. Rubb. Res., (2000), 3(4):214-221.

Pan, Zhiqiang et al., "The Major Protein of Guayule Rubber Particles is a Cytochrome P450: Characterization Based on cDNA Cloning and Spectroscopic Analysis of the Solubilized Enzyme and Its Reaction Products," The Journal of Biological Chemistry, (1995), 270(15):8487-8494.

Pan, Zhiqiang et al., "Aspirin Inhibition and Acetylation of the Plant Cytochrome P450, Allene Oxide Synthase, Resembles that of Animal Prostaglandin Endoperoxide H Synthase," The Journal of Biological Chemistry, (1998), 273 (29):18139-18145.

Pfaff, Michael W. et al., "A new mathematical model for relative quantification in real-time RT-PCR," Oxford University Press:Nucleic Acids Research, (2001), 29(900):2001-2007.

\* cited by examiner

FIG. 1

```
Guayule CPTL   MDLVAESQKFFRRTSQSGSIVLFLLMHVVHLTISVLYIVREIFRAIESYLITNGYVK  (SEQ ID NO: 3)
               ||||  |   ||  |  ||||  ||||| |||| |||||  ||||||||| ||||||
Lettuce CPTL2  MDLVGGPQKILHKISLNDHMILLLMWHILHLIVQVIYFVWEKMRAIESYLIANGIVK  (SEQ ID NO: 4)

Guayule CPTL   TYTNINLQRVKYLGIVVDSDEARNISKVVELLEWLSAIGVKKKICLYDREGVLKKSKA  (SEQ ID NO: 3)
               || |||  |||||||||||||| | || |||||| |  ||||| ||||||||||| 
Lettuce CPTL2  TYEDLNLDRVKYLGIVVDSDEARETSKVIELLEWISDIGVKKVCLYDREGVLKKSKE  (SEQ ID NO: 4)

Guayule CPTL   VIMERFGSTETSNDSAVANPLSKKRMDFEFVSITDGKEAVAKAANLLFKKYYVDEDS  (SEQ ID NO: 3)
                 |  |               | ||||||||||||| |||||||| |||||| |  
Lettuce CPTL2  LFMEKFDSMENSE------TNQKRKMDFEFVSIVDGKETVAKAANLLYKKYYSDPNS  (SEQ ID NO: 4)

Guayule CPTL   EKPFFTETHLTEALKTLGQVEPDPDLLLIYGPVRCHLGFPAWRLRYTEMVHMGPLKY  (SEQ ID NO: 3)
               ||||||| ||||| |||| || ||||||||| |||||||||| ||||||||| | |
Lettuce CPTL2  EKPFFTETYLTEALRILGSNEPDPDLILIYGPTRCHLGFPAWRIRYTEMVHMGSLKN  (SEQ ID NO: 4)

Guayule CPTL   KKFGLILKAIHRFTKVKQNYGS*  (SEQ ID NO: 3)
               |||||||||| | ||||||||||
Lettuce CPTL2  KKFGLILKAINKYTKVKQNYGS*  (SEQ ID NO: 4)
```

FIG. 2

```
Guayule CPTL      MDLVAESQKFFRRTSQSGSIVLFLLMWHVVHLTISVLYIVREIFRAIESYLITNGYVK  (SEQ ID NO: 3)
                  ||| ||   |||   |||||||||  ||||| ||||||  ||  |||  ||| ||
Dandelion TbRta   MDLLDGPQKIYRKISQNENIVLLLMWHVLHLIIKFMYFVREILRGIENYLIINEIVK  (SEQ ID NO: 5)

Guayule CPTL      TYTNINLQRVKYLGIVVDSDEARNISKVVELLEWLSAIGVKKICLYDREGVLKKSKA  (SEQ ID NO: 3)
                  || ||||||||||||||||||||| |||||||||||||| |||||||||||||||
Dandelion TbRta   TYEDLNLNRVKYLGIVVDSDEARETSKVIELLEWLSDIGVKKVCLYDREGVLKKSKE  (SEQ ID NO: 5)

Guayule CPTL      VIMERFGSTETSNDSAVANPLSKKRMDFEFVSITDGKEAVAKAANLLFKKYYVDEDS  (SEQ ID NO: 3)
                  |  |||    |||            |||||||| ||||| |||||| ||||| |
Dandelion TbRta   VFMEKFDSMENSD------VDHKRKMEFEFVSIIDGKETVAKAANLLNKKYYSDANT  (SEQ ID NO: 5)

Guayule CPTL      EKPFFTETHLTEALKTLGQVEPDPDLLLIYGPVRCHLGFPAWRLRYTEMVHMGPLKY  (SEQ ID NO: 3)
                  |||||||| |||||  |   |||||||||||| ||||||||| ||||||||||  |
Dandelion TbRta   EKPFFTETYLTEALRILGANEPDPDLLLIYGPTRCHLGFPAWRIRYTEMVHMGSLKN  (SEQ ID NO: 5)

Guayule CPTL      KKFGLILKAIHRFTKVKQNYGS*  (SEQ ID NO: 3)
                  ||  || |||| ||||||||||
Dandelion TbRta   KKLGLIFKAINKYTKVKQNYGS*  (SEQ ID NO: 5)
```

FIG. 3A

```
Guayule CPTL    ATGGATCTAGTAGCTGAATCACAGAAGTTTTTCGCAGGACCTCGCAGAGTGGCAGCAT  (SEQ ID NO: 2)
                ||||||||| || |||||| || |||||| |||| || ||  |  |||  ||||||
Lettuce CPTL2   ATGGATCTCGTAGGTGGACCCCAGAAGATTTTACACAAAATCTCACTGAATGATCACAT  (SEQ ID NO: 6)

Guayule CPTL    TGTGCTCTTCTTGCTCTGGCATGTAGTTCACTTAACAATCAGTGTTTTATACATTGTCC  (SEQ ID NO: 2)
                 || |||||  ||| ||||||| |||  ||||| |||  ||| || | ||||| |||
Lettuce CPTL2   GATACTTCTGTTGCTGTGGCACATTCTTCATTTAATTGTTCAAGTCATATACTTTGTTT  (SEQ ID NO: 6)

Guayule CPTL    GGGAGATCTTTCGTGCGATTGAAAGCTACCTTATAACAAACGGATATGTGAAAACATAC  (SEQ ID NO: 2)
                |||||| | ||| ||  ||||||||| || |||||| ||| |||  |||||||||||
Lettuce CPTL2   GGGAGAAGATGCGTGCAATTGAAAGCTATCTTATAGCAAATGGAATTGTCAAAACATAT  (SEQ ID NO: 6)

Guayule CPTL    ACAAATATAAATTTACAACGGGTCAAATATCTTGGAATTGTTGTGGACAGTGATGAAGC  (SEQ ID NO: 2)
                 |  || | ||||| ||| ||| |||||||| ||||||||||| ||||| |||||||
Lettuce CPTL2   GAAGATCTGAATTTAGAGACAGAGTGAAGTATCTTGGATATAGTGTGGTGGATAGTGATGAAGC  (SEQ ID NO: 6)

Guayule CPTL    CCGTAACATCTCAAAAGTGGTTGAACTTTTTAGAGTGGCTTTCAGCTATAGGTGTGAAAA  (SEQ ID NO: 2)
                 ||| || ||||||||||| ||| |||| ||| |||| ||||| |||| |||||||||
Lettuce CPTL2   TCGTGAAACCTCAAAAGTTATTGAACTTTTTGGAGTGGATTTCAGATATATTGGTGTGAAAA  (SEQ ID NO: 6)

Guayule CPTL    AGATCTGTCTTTATGACCGGGAAGGAGTGTTGAAGAAGTCA  (SEQ ID NO: 2)
                || |||||| ||||||||  |||| ||||||||||||||||
Lettuce CPTL2   AGGTCTGCCTTTATGACAGAGAAGGAGTGTTGAAGAAGTCC  (SEQ ID NO: 6)
```

FIG. 3B

```
Guayule CPTL   AAGGCGGTCATCATGGAGAGATTTGGCTCTACAGAGACTTCCAATGATAGTGCAGTAGC (SEQ ID NO: 2)
               |||| |||| ||||||||||||| |||||| || |||  |||||| |||||
Lettuce CPTL2  AAGGAACTGTTCATGGAGAGAATTTGATTCTATGGAGAATTC--------AGAAAC   (SEQ ID NO: 6)

Guayule CPTL   CAATCCACTAAGTAAAAAAACGGATGGATTTGTTTCAATCACTGATGGCAAAG      (SEQ ID NO: 2)
               |||||| ||||||| ||||           |||||| ||  ||||  |||||
Lettuce CPTL2  CAATCAAAAAAGGAAAA------TGGATTTTGAATTTGTTTCAATCGTTGATGGAAAAG (SEQ ID NO: 6)

Guayule CPTL   AAGCAGTTGCTAAAGCAGCTAACCTACTCTTTAAAAAATATTATGTGGACGAAGAATCA (SEQ ID NO: 2)
               ||||||||||||| |||||||| |||| |||||||||| ||||| |||| ||||| ||
Lettuce CPTL2  AAACAGTTGCTAAAGCAGCGAATCTGCTAAATCTTGCTATATAAAAAGTATTATTCTGATCCAAATTCA (SEQ ID NO: 6)

Guayule CPTL   GAAAAACCATTCTTTACTGAAACCCACTTGACCGAGGCACTAAAGACCCCTCGGGCAAGT (SEQ ID NO: 2)
               |||||||||||||||||||| |||| ||||| ||||||||||| || |||
Lettuce CPTL2  GAAAAACCATTCTTTACTGAAACCTATTTGACCGAAGCACTTAGGATCCTAGGTTCTAA  (SEQ ID NO: 6)

Guayule CPTL   AGAGCCAGATCCCGATCTCTTTTATTAATTTACGGGCCAGTGAGGTGCCACCTTGGTTTTC (SEQ ID NO: 2)
               |||||| ||||| ||||| |||||  ||||||||   ||| || ||||||||||||||
Lettuce CPTL2  TGAGCCGGATCCTGATCTTATACTGATTTATGGGCCCACAAGGTGCCACCTTGGTTTTC  (SEQ ID NO: 6)

Guayule CPTL   CAGCCATGGCGACTTCGTTACACGGAGATGGTGCACATGGGACCATTAAAGTACAAGAAA (SEQ ID NO: 2)
               ||||||||| |  ||||| |||||| ||||||| |||| ||||||||| ||| ||| ||
Lettuce CPTL2  CAGCCATGGCGTATTCGTTATACAGAGATGGTACACATGGTACACATGGGATCATTGAAGAACAAGAAG (SEQ ID NO: 6)

Guayule CPTL   TTTGGTTTGATTCTGAAAGCAATTCACAGGTTCACTAAGGTGAAGCAAAACTATGGTTC  (SEQ ID NO: 2)
               ||||||||||||| |||||  || ||||||  |||| ||||||||||||||| |||||
Lettuce CPTL2  TTTGGTTTGATTTTGATTTTGAAAGCCATCAACAAATACACCAAGGTGAAGCAGAACTACGGTTC (SEQ ID NO: 6)

Guayule CPTL   ATAA (SEQ ID NO: 2)
               |||
Lettuce CPTL2  TTAA (SEQ ID NO: 6)
```

FIG. 4A

```
Guayule CPTL     ATGGATCTTAGTAGCTGAATCACAGAAGTTTTTCGCAGGACCTCGCAGAGTGGCAGC  (SEQ ID NO: 2)
                 ||||||||   |||    |||| ||||| |||| |||   ||||||  ||||||  
Dandelion TbRta  ATGGATCTGTTAGACGGACCCCAGAAGATTTATCGCAAAATCTCACAGAATGAGAAC  (SEQ ID NO: 7)

Guayule CPTL     ATTGTGCTCTTCTTGCCTCTCTGGCATGTAGTTCACTTAACAATCAGTGTTTTATACATT  (SEQ ID NO: 2)
                 ||  || ||  ||| || |||||||||||  |||  ||||  ||||||| |||| |||
Dandelion TbRta  ATCGTGCTATTGTTGCTGTGGCATGTTCTTCATTTAATTATCAAATTTATGTACTTT   (SEQ ID NO: 7)

Guayule CPTL     GTCCGGGAGATCTTTCGTGCGATTGAAAAGCTACCTTATAACAAACGGATATGTGAAA   (SEQ ID NO: 2)
                 || ||||||||| || || || |||||  |||||  ||||| ||| |||| ||||||
Dandelion TbRta  GTTCGCGAGATCTTACGTGAATTGAAATTGAAAACTATCTTTATAATGAAATTGTGAAA  (SEQ ID NO: 7)

Guayule CPTL     ACATACACAAATATAAATTTACAACGGGTCAAATATCTTGGAATTGTTGTGTGGACAGT  (SEQ ID NO: 2)
                 ||||| ||||||| |||  |||||  ||||||||||||||||||||| ||||||||||
Dandelion TbRta  ACATATGAAGATCTGAATTTAAAACAGAGTGAAAATATCTTGGAGTGTTGGTGGACAGT  (SEQ ID NO: 7)

Guayule CPTL     GATGAAGCCCGTAACATCTCAAAAGTGGTTGAACTTTTTAGAGTGGCTTTCAGCTATA   (SEQ ID NO: 2)
                 |||||||| ||||  ||| |||||||| |||||||| |||||||| ||||||||| ||
Dandelion TbRta  GATGAAGCACGTGAAACTTCAAAAGTTATTGAACTTTTTGGAGTGGCTTTCAGATATT  (SEQ ID NO: 7)

Guayule CPTL     GGTGTGAAAAAGATCTGTCTTTATGACCGGAAGGAGTGTTGAAGAAGTCAAAGGCG    (SEQ ID NO: 2)
                 |||||||||||| ||||  |||||||| |||||||||| ||||||| |||| ||
Dandelion TbRta  GGTGTGAAAAAAGTGTGCCTTTATGACCGTGAAGGAGTGTTGAAGAAATCCATAAAA  (SEQ ID NO: 7)

Guayule CPTL     GTCATCATGGAGAGATTTGGCTCTACAGAGACTTCCAATGATAGTGCAGTAGCCAAT    (SEQ ID NO: 2)
                 ||||| |||||||||| |||| || |||||  |  ||||| ||||||||  ||| 
Dandelion TbRta  AAGGAAGTGTTCATGGAGAAATTTGATTCTATGGAGAATTCGGATGTTGATC-----   (SEQ ID NO: 7)
```

FIG. 4B

```
Guayule CPTL      CCACTAAGTAAAAAAACGGATGGATTTTGAATTTGTTTCAATCACTGATGATGGCAAAGAA (SEQ ID NO: 2)
                                                ||||||||||| ||||||| |||||||
Dandelion TbRta   ---------------GGAAAATGGAATTTGAATTTGTTTCAATTATTGATGGAAAAGAA (SEQ ID NO: 7)

Guayule CPTL      GCAGTTGCTAAAGCAGCTAACCTACTCTTTAAAAATATTATGTGGACGAAGAATCA (SEQ ID NO: 2)
                   |||||||||||||||| ||  || || |||||| |||| | | ||  ||
Dandelion TbRta   ACAGTTGCTAAAGCTGCAAACCTTCTAAACAAAAAATATTATTCAGATGCAAATACA (SEQ ID NO: 7)

Guayule CPTL      GAAAAACCATTCTTTACTGAAACCCACTTGACCGAGGCACTAAAGACCCTCGGGCAA (SEQ ID NO: 2)
                  |||||| |||| ||||| ||||||| |||||||||||||||| ||  ||| |||||
Dandelion TbRta   GAAAAACCGTTCTTTACTTGAAACCTACTTGACCGAGGCACTCAGGATCTTAGGTGCT (SEQ ID NO: 7)

Guayule CPTL      GTAGAGCCAGATCCCGATCTTTTTATTAATTTACGGGCCAGTGAGGTGCCACCTTGGT (SEQ ID NO: 2)
                   | |||||||||||| |||||| ||| ||||| |||||||| |||||||||||||| |
Dandelion TbRta   AATGAGCCAGATCCTGATCTTTTACTGATCTATGGCCCCACAAGGTGCCACCTTGGA (SEQ ID NO: 7)

Guayule CPTL      TTTCCAGCATGGGCGACTTCGTTACACGGAGAGATGGTGCACATGGGACCATTAAAGTAC (SEQ ID NO: 2)
                  ||||||||||||| ||  |||||| || ||||||| ||| ||||| |||| |||| ||
Dandelion TbRta   TTTCCAGCATGGGCGAATTCGTTATACAGAGATGGTACACATGGGATCACTGAAGAAC (SEQ ID NO: 7)

Guayule CPTL      AAGAAATTTGGTTTGATTCTGAAAGCAATTCACACAGGTTCACTAAGGTGAAGCAAAAAC (SEQ ID NO: 2)
                  ||||||||| |||| ||| ||||||| |||||| | |||   || ||||||||||| ||
Dandelion TbRta   AAGAAATTAGGTTTGATTTTCAAAGCCATTAACAAATACACTAAGGTGAAGCAGAAC (SEQ ID NO: 7)

Guayule CPTL      TATGGTTCATAA (SEQ ID NO: 2)
                  || ||||||||
Dandelion TbRta   TACGGTTCATAA (SEQ ID NO: 7)
```

GENETICALLY ALTERED GUAYULE HAVING INCREASED RUBBER PRODUCTION AND METHODS THEREOF

CROSS REFERENCE TO RELATED APPLICATIONS

This patent application claims priority to U.S. Patent Application 62/560,323 filed on Sep. 19, 2017, contents of which are expressly incorporated by reference herein.

BACKGROUND OF THE INVENTION

Sequence Listing

The Sequence Listing submitted via EFS-Web as ASCII compliant text file format (.txt) filed on Sep. 10, 2018, named "SequenceListing_ST25", (created on Aug. 31, 2017, 34 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

FIELD OF THE INVENTION

This invention relates to methods of increasing the rubber production in a genetically altered guayule by overexpression of a recombinant plant polynucleotide. The invention also relates to a genetically altered guayule that produce increased amount of rubber than is produced by a wild-type guayule.

DESCRIPTION OF RELATED ART

This section provides background information to the present disclosure which is not necessarily prior art.

Natural rubber, cis-1,4 polyisoprene, a biobased elastomer, is produced primarily in tropical climates by the Brazilian rubber tree, *Hevea brasiliensis* (*Hevea*). Natural rubber is essential in many industrial applications and in many of its most significant applications, natural rubber cannot be replaced by synthetic alternatives. Because of its desirable properties and heavy demand, the price of natural rubber is rising, making natural rubber increasingly more precious as an industrial material.

Natural rubber is unique in that for many applications it has no synthetic equivalent. Indeed, its unique properties of resilience, elasticity, abrasion- and impact-resistance, efficient heat dispersion, and malleability at cold temperatures are unmatched by synthetic alternatives (Cornish, *Phytochemistry* 57, 1123-1134 (2001)). For example airplanes cannot safely land with tires made from synthetic rubber; and only truck tires made from natural rubber are resilient enough to withstand heavy shear and loads. Thus, potential shortages of natural rubber foretell profound consequences for commerce.

Unfortunately, today, *Hevea brasiliensis* is essentially the sole commercial source of natural rubber. But, fortunately, there are alternative plant sources for natural rubber. Chief among the alternatives is guayule (*Parthenium argentatum* Gray). Guayule, is a shrub in the family Asteraceae, native to the southwestern United States and northern Mexico.

On its own, guayule is presently not economical without either greater rubber yields or identification and development of high value coproducts. However, if developed, guayule has great potential as a new or alternative crop for arid and semiarid areas of the southwestern United States, north central Mexico, and regions with similar climates around the world. See, e.g., Thompson and Ray *Breeding Guayule*, p 93-165, in *Plant Breeding Reviews*, John Wiley & Sons, Inc. (1989); Wright, et al., *Guayule economics*, p 351-366, in *Guayule natural rubber*, Whitworth and Whitehead (eds.), Office of Arid Lands, Univ. of Arizona, Tucson (1991)). Thus, development of guayule cultivars capable of producing high yields of natural rubber latex would be invaluable for increasing the quantities of natural latex rubber.

Therefore, a need exists for methods for improving the quantity and/or quality of natural rubber from guayule, and genetically altered guayule that produces increased amount of rubber compared to the wild-type guayule.

However, attempts to increase rubber production in guayule through the rubber biosynthetic pathway by manipulation of specific enzyme levels are fraught with difficulty. In general, control of rubber production is not determined by a single "rate limiting step", rather individual components are associated with control coefficients determined empirically (see, e.g., Kacser and Burns (1973) *Sympo. Soc. for Exper. Bio.* 27:65-104). In addition, it is difficult to determine the effective concentrations of pathway intermediates in the tissue/cells/compartments where the reactions are occurring. Given the complex nature of the rubber biosynthetic pathway, one of ordinary skill in the art cannot have a reasonable expectation of success for increasing rubber biosynthesis by increasing the amount of any one enzyme in the rubber biosynthetic pathway. However, it is known that decreasing cis-prenyltransferase (Cpt) components in some plants can result in decreased rubber biosynthesis.

More recently, in a preprint article in bioRxiv (the preprint server for Biology), Lakusta, et al., (dx.doi.org/10.1101/384149; Aug. 3, 2018) identified three guayule genes encoding Cpt (PaCpt) and one guayule gene encoding a cis-prenyltransferase binding protein (PaCbp). Lakusta, et al., found that co-expression of PaCBP with each individual PaCpt genes resulted in PaCpt-PaCbp hetero-protein complexes formation and that these hetero-protein complexes incorporated, in-vitro, isopentenyl diphosphate into dehydrodolichyl diphosphates (part of the rubber biosynthetic pathway). Also, U.S. Patent App. Pub. 2018/0127767 (Scheller et al) described a guayule transcription factor gene (CBF/DREB) that, when overexpressed in *Nicothiana benthamiana* or lettuce leaves, increased expression of genes involved in the rubber biosynthetic pathway. But, no increase in rubber production was demonstrated.

There is a need in the art for methods for improving the quantity and/or quality of natural rubber produced by guayule, and a need for genetically altered guayule capable of producing increased amount of natural rubber latex compared to the amount of rubber produced by wild-type guayule. The present invention, different from the related art, provides such methods and guayule.

BRIEF SUMMARY OF THE INVENTION

It is an object of this invention to have a cDNA or polynucleotide having the sequence of SEQ ID NO: 1, SEQ ID NO: 2, or a sequence at least 80%, at least 85%, at least 90%, or at least 95% identical to SEQ ID NO: 1 or 2, and which encodes cis-prenyltransferase-like (Cptl), a protein that activates cis-prenyltransferase (Cpt). Guayule Cptl (cis-prenyltransferase-like) has an amino acid sequence of SEQ ID NO: 3 or an amino acid sequence at least 80%, at least 85%, at least 90%, or at least 95% identical to SEQ ID NO: 3 and still activates Cpt. It is another object of this invention to have an expression vector containing a heterologous promoter operably linked to this cDNA. The heterologous promoter can be a cold-inducible promoter (e.g cold regulated 15a (Cor15a), cold regulated 39 (Cor39), WRKY71, wheat cold specific 120 (Wcs120), rare cold inducible 2A/2B (RCI2A/RCI2B), C-repeat binding factors (CBFs)) or a tissue-specific promoter (e.g., a phloem-specific promoter (e.g., Glycine-rich cell wall protein (GRP) 1.8 promoter, *Arabidopsis thaliana* sucrose transport 1 or 2 (AtSUC1 or AtSUC2) promoter, citrus phloem protein 2 (CsPP2) promoter, *Arabidopsis thaliana* phloem protein (AtPP2) promoter, and citrus phloem promoter small cyclic amphipathic protein 396SS). It is a further object of this invention to have a transformed cell containing this expression vector. The transformed cell can be a plant cell (such as guayule), fungus cell, or bacterial cell. It is another object of this invention to have a genetically altered guayule containing this expression vector or an expression vector having a heterologous promoter operably linked to this cDNA. It is a further object of this invention that this genetically altered guayule has increased mRNA levels for the protein that activates Cpt and is encoded by this cDNA than Cptl mRNA levels in a wild-type guayule. It is another object of this invention that the genetically altered guayule containing the expression vector produces increased amount of Cptl compared to the amount of Cptl produced by wild-type guayule and that this increased amount of Cptl results in the genetically altered guayule producing increased amount of rubber than is produced by wild-type guayule. It is another object of this invention that this genetically altered guayule produces increased amount of rubber compared to the amount of rubber produced by a wild-type guayule. Another object of this invention is the rubber produced by this genetically altered guayule. Further objects of this invention include having a germplasm of the genetically altered guayule and having at least one seed of the genetically altered guayule.

It is another object of this invention to have an expression vector containing a heterologous promoter operably linked to a polynucleotide which encodes a protein, the protein having an amino acid sequence of SEQ ID NO: 3 (guayule Cptl) or a sequence that is at least 80%, at least 85%, at least 90%, or at least 95% identical to SEQ ID NO: 3. This encoded protein activates Cpt and is called cis-prenyltransferase-like (Cptl). The heterologous promoter can be a cold-inducible promoter (e.g., cor15a, cor39, WRKY71, wcs120, RCI2A, RCI2B, and CBF2) or a tissue-specific promoter (e.g., a phloem-specific promoter (e.g., GRP 1.8 promoter, AtSUC1 promoter, AtSUC2 promoter, CsPP2 promoter, AtPP2 promoter, and citrus phloem promoter 396SS). It is a further object of this invention to have a transformed cell containing this expression vector. The transformed cell can be a plant cell (such as guayule), fungus cell, or bacterial cell. It is another object of this invention to have a genetically altered guayule containing this expression vector. It is a further object of this invention that this genetically altered guayule has increased mRNA levels of the protein that activates Cpt and is encoded by this polynucleotide than Cptl mRNA levels in a wild-type guayule. It is another object of this invention that the genetically altered guayule containing the expression vector produces increased amount of Cptl compared to the amount of Cptl produced by wild-type guayule and that this increased amount of Cptl results in the genetically altered guayule producing increased amount of rubber than is produced by wild-type guayule. It is another object of this invention that this genetically altered guayule produces increased amount of rubber compared to the amount of rubber produced by a wild-type guayule. Another object of this invention is the rubber produced by this genetically altered guayule. Further objects of this invention include having a germplasm of the genetically altered guayule and having at least one seed of the genetically altered guayule.

It is an object of this invention to have a method of increasing the amount of rubber produced by a genetically altered guayule compared to the amount of rubber produced by wild-type guayule by (i) transforming a wild-type guayule cell with an expression vector containing a heterologous promoter operably linked to a polynucleotide encoding a protein having the amino acid sequence of SEQ ID NO: 3 or a sequence at least 80%, at least 85%, at least 90%, or at least 95% identical to SEQ ID NO: 3 to produce a transformed guayule cell, such that the protein (Cptl) activates Cpt (the heterologous promoter can be a cold-inducible promoter (e.g., cor15a, cor39, WRKY71, wcs120, RCI2A, RCI2B, and CBF2) or a tissue-specific promoter (e.g., a phloem-specific promoter (e.g., GRP 1.8 promoter, AtSUC1 promoter, AtSUC2 promoter, CsPP2 promoter, AtPP2 promoter, and citrus phloem promoter 396SS); (ii) selecting for a transformed guayule cell that produces an increased amount of the protein (Cptl) that activates Cpt than is produced by wild-type guayule to provide a genetically altered guayule cell, and (iii) growing the genetically altered guayule cell into a genetically altered guayule, such that the genetically altered guayule produces increased amount of the protein (Cptl) having the amino acid sequence of SEQ ID NO: 3 or a sequence at least 80%, at least 85%, at least 90%, or at least 95% identical to SEQ ID NO: 3, and which activates Cpt, compared to the amount of protein (Cptl) produced by wild-type guayule, and the genetically altered guayule produces increased amount of rubber compared to the amount of rubber produced by wild-type guayule because of the increased amount of protein (Cptl) that activates Cpt compared to the amount produced by wild-type guayule. The polynucleotide can have a DNA sequence of SEQ ID NO: 1, SEQ ID NO: 2, or a sequence at least 80%, at least 85%, at least 90%, or at least 95% identical to SEQ ID NO: 1 or 2. It is another object of this invention to have a genetically altered guayule or part thereof (germplasm, rubber, seed, leaf, root, stem, pollen, flower, etc.) produced by this method.

It is another object of this invention to have a method of increasing the amount of rubber produced by a genetically altered guayule compared to the amount of rubber produced by wild-type guayule by (i) transforming a wild-type guayule cell with an expression vector such that the expression vector has a heterologous promoter linked to a cDNA of SEQ ID NO:1 or 2 or a sequence at least 80%, at least 85%, at least 90%, or at least 95% identical to SEQ ID NO: 1 or 2 to produce a transformed guayule cell and which encodes a Cpt activating protein (Cptl) (the heterologous promoter can be a cold-inducible promoter (e.g., cor15a, cor39, WRKY71, wcs120, RCI2A, RCI2B, and CBF2) or a tissue-specific promoter (e.g., a phloem-specific promoter (e.g., GRP 1.8 promoter, AtSUC1 promoter, AtSUC2 promoter, CsPP2 promoter, AtPP2 promoter, and citrus phloem promoter 396SS); (ii) selecting for a transformed guayule cell that produces an increased amount of the Cpt activating protein (Cptl) than is produced by wild-type guayule to provide a genetically altered guayule cell, and (iii) growing the genetically altered guayule cell into a genetically altered guayule, such that this genetically altered guayule contains the cDNA or polynucleotide, the genetically altered guayule produces increased amount of the Cpt activating protein (Cptl) compared to the amount produced by wild-type guayule, and the genetically altered guayule produces increased amount of rubber than the amount of rubber produced by a wild-type guayule because of the increased amount of Cpt activating protein (Cptl) in the genetically altered guayule. The cDNA encodes a protein having an amino acid sequence of SEQ ID NO: 3 or a sequence at least 80%, at least 85%, at least 90%, or at least 95% identical to SEQ ID NO: 3. It is another object of this invention to have a genetically altered guayule or part thereof (germplasm, rubber, seed, leaf, root, stem, pollen, flower, etc.) produced by this method.

BRIEF DESCRIPTION OF THE SEVERAL VIEWS OF THE DRAWINGS

FIG. 1 shows an alignment of guayule Cptl and lettuce cis-prenyltransferase-like 2 (Cptl2) amino acid sequences (SEQ ID NOs: 3 and 4 respectively).

FIG. 2 shows an alignment of guayule Cptl and dandelion rubber transferase activator (TrBta) amino acid sequences (SEQ ID NOs: 3 and 5 respectively).

FIG. 3A and FIG. 3B show an alignment of guayule Cptl and lettuce Cptl2 coding sequences (cds) (SEQ ID NOs: 2 and 6 respectively).

FIG. 4A and FIG. 4B show an alignment of guayule Cptl and dandelion TrBta cds sequences (SEQ ID NOs: 2 and 7 respectively).

DETAILED DESCRIPTION OF THE INVENTION

Figure 5:
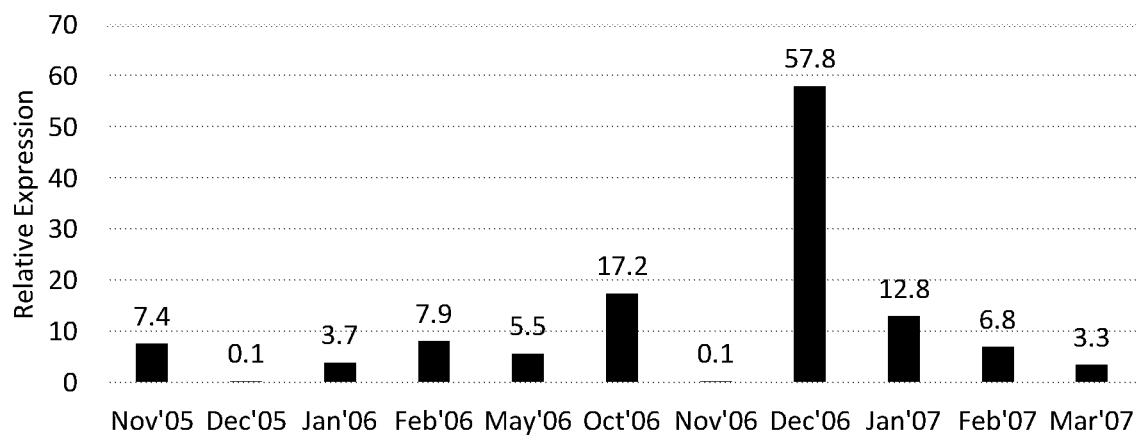
FIG. 5 shows relative expression of CPTL in field-grown guayule over different months of the year.

This invention involves the identification of a gene (Cptl) in guayule encoding a cis-prenyltransferase-like (Cptl) protein similar to the cis-prenyltransferase-like 2 (Cptl2) protein in lettuce (*Lactuca sativa*) and to the rubber transferase activator (TbRta) in dandelion (*Taraxacum brevicorniculatum*). Cptl2 in lettuce and the TbRta protein in dandelion are involved in rubber biosynthesis. Qu, et al. (2015) *J. Biol. Chem.* 290(4):1898-1914 described lettuce Cptl2 is a scaffolding, non-enzymatic protein that tethers cis-prenyltransferase 3 (Cpt3) onto the endoplasmic reticulum and is necessary for rubber biosynthesis. Qu, et al., also described lettuce Cptl2 as being similar to human Nogo-B. Qu, et al., demonstrated that RNAi reduction of lettuce Cptl2 decreases natural rubber levels in lettuce; the reduction in natural rubber levels is approximately linear with the reduction of Cptl2 expression; and yet there is no effect on the rubber's molecular weight. Qu, et al., concluded that Cptl2 is 'necessary but not sufficient' for rubber production. Epping, et al., *Nat. Plants* 1(5) (2015) described dandelion TbRTA as a Nogo-B homolog which interacts with Cpt on the endoplasmic reticulum. Epping, et al., reported that knocking out TrRta expression either eliminated rubber biosynthesis or reduced it to such a low level that it is difficult to detect. Epping, et al., described residual isoprenoids as dolichols but lacked data demonstrating it. Yet, neither Epping, et al., nor Qu, et al., described overexpression of TrRta or Cptl2, respectively, as increasing rubber production. This silence on examining the impact of overexpression of these genes could possibly stem from their inability to find a difference in rubber production when these genes are overexpressed, compared to the amount of rubber produced in the wild-type plants. Further, nobody else has reported that increasing the amount of these proteins resulted in an increase in rubber production in lettuce or dandelion.

At the amino acid level, guayule Cptl has 70% identity to lettuce Cptl2 (see FIG. 1) and 71% identity to dandelion TbRta (see FIG. 2). At the DNA level, the cds for guayule Cptl has 76% identity to the cds for lettuce Cpt/2 (see FIG. 3A and FIG. 3B) and 77% identity to the cds for TbRta (see FIG. 4A and FIG. 4B). In contrast to lettuce for which two related Cptl cDNAs have been identified, guayule contains as single Cptl gene both in the assembled genome and the available EST database. Guayule Cptl has an unexpected structure compared to the structure of cis-prenyltransferase (Cpt) genes in many other plants. Cpt genes are usually transcribed as a single unit, without introns, in other plants. In contrast, guayule Cptl is encoded on 8 exons separated by 7 introns. The cDNA sequence of guayule Cptl is in SEQ ID NO: 1. Guayule Cptl coding sequence (cds) is nucleotides 74-826 of SEQ ID NO: 1, and is the entire sequence of SEQ ID NO: 2. Table 1, infra, lists the sequence identification numbers of some of the sequences discussed herein. Not wishing to be bound to any particular hypothesis, guayule Cptl can bind to rubber particles, can bind to cis-prenyltransferase (Cpt), can anchor Cpt to a cell's endoplasmic reticulum, and can activate Cpt. Thus, increasing the amount of Cptl results in activating more Cpt and increasing rubber biosynthesis.

TABLE 1

| Name | SEQ ID NO |
| --- | --- |
| Guayule Cptl cDNA | SEQ ID NO: 1 |
| Guayule Cptl cds (DNA) | SEQ ID NO: 2 |
| Guayule Cptl (amino acid) | SEQ ID NO: 3 |
| Lettuce CPTL2 (amino acid) | SEQ ID NO: 4 |
| Dandelion TbRta (amino acid) | SEQ ID NO: 5 |
| Lettuce Cptl2 cds (DNA) | SEQ ID NO: 6 |
| Dandelion TbRta cds (DNA) | SEQ ID NO: 7 |

Because this invention involves production of genetically altered plants and involves recombinant DNA techniques, the following definitions are provided to assist in describing this invention.

The term "transgenic plant" as used herein refers to a plant comprising at least one heterologous nucleic acid sequence that was introduced into the plant at some point in its lineage by genetic engineering techniques. In an exemplary embodiment, a transgenic plant is a guayule plant that is transformed with an expression vector containing, at least, a heterologous promoter operable linked to a polynucleotide which encodes a Cpt activating protein. In another exemplary embodiment, a transgenic plant is a plant that is the progeny or descendant of a plant that is transformed with an expression vector containing, at least, a heterologous promoter operable linked to a polynucleotide which encodes a Cpt activating protein and which contains, at least, the expression vector comprising a heterologous promoter operable linked to a polynucleotide which encodes a Cpt activating protein. Thus, the term "transgenic plant" refers to plants which are the direct result of transformation with a heterologous nucleic acid or transgene, and the progeny and descendants of transformed plants which contains, at least, the introduced heterologous nucleic acid or transgene.

The expression "produces increased amount of rubber" as used herein refers to the rubber content produced by the transformed guayule of the invention compared to the rubber content produced by a wild-type guayule.

The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60% N, about 70% or about 80% and the upper end of the range of purity is more than 90%, about 90%, or about 80%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences. Individual nucleotides are referred to as "nt".

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., *J. Biol. Chem.* 260:2605-2608 (1985); and Rossolini et al., *Mol. Cell. Probes* 8:91-98(1994)). Because the amino acid sequence of SEQ ID NO: 3 is described herein, one can chemically synthesize a polynucleotide which encodes these enzymes. Because of the degeneracy of nucleic acid codons, one can use various different polynucleotides to encode identical proteins. Table 2, infra, contains information about which nucleic acid codons encode which amino acids.

TABLE 2

| Amino acid | Nucleic acid codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, ACT, AGC |
| Thr/T | ACT, ACC, ACA, ACG |
| Trp/W | TGG |
| Tyr/Y | TAT, TAC |
| Val/V | GTT, GTC, GTA, GTG |

In addition to the degenerate nature of the nucleotide codons which encode amino acids, alterations in a polynucleotide that result in the production of a chemically equivalent amino acid at a given site, but do not affect the functional properties of the encoded protein, are well known in the art. "Conservative amino acid substitutions" are those substitutions that are predicted to interfere least with the properties of the reference protein. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 3 provides a list of exemplary conservative amino acid substitutions. Conservative amino acid substitutions generally maintain (a) the structure of the protein backbone in the area of the substitution, for example, as a beta sheet or alpha helical conformation, (b) the charge or hydrophobicity of the molecule at the site of the substitution, and/or (c) the bulk of the side chain.

TABLE 3

| Amino Acid | Conservative Substitute |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Ile, Leu |
| Phe | His, Leu, Met, Trp, Tyr |
| Ser | Cys, Thr |

TABLE 3-continued

| Amino Acid | Conservative Substitute |
| --- | --- |
| Thr | Ser, Val |
| Trp | Phe, Tyr |
| Tyr | His, Phe, Trp |
| Val | Ile, Leu, Thr |

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The terms "identical" or percent "identity", in the context of two or more nucleic acids or polypeptide sequences, refer to two or more sequences or subsequences that are the same or have a specified percentage of amino acid residues or nucleotides that are the same (e.g., 80% identity, 85% identity, 90% identity, 99%, or 100% identity), when compared and aligned for maximum correspondence over a designated region as measured using a sequence comparison algorithm or by manual alignment and visual inspection.

The phrase "high percent identical" or "high percent identity", in the context of two polynucleotides or polypeptides, refers to two or more sequences or subsequences that have at least about 80%, identity, at least about 81%, 820%, 83%, 84%, 85%, 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, a high percent identity exists over a region of the sequences that is at least about 50 residues in length. In another exemplary embodiment, a high percent identity exists over a region of the sequences that is at least about 100 residues in length. In still another exemplary embodiment, a high percent identity exists over a region of the sequences that is at least about 150 residues or more in length. In one exemplary embodiment, the sequences are high percent identical over the entire length of the nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al. (eds.), *Current Protocols in Molecular Biology*, 1995 supplement).

The term "heterologous" when used with reference to portions of a nucleic acid indicates that the nucleic acid contains two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature such as a fusion protein.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

A genetically altered organism is any organism with any change to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has changes in its DNA caused by the one or more mutagens, as compared to the wild-type organism (i.e, organism not subjected to the mutagens). Also, an organism that has been bred to incorporate a mutation into its genetic material is a genetically altered organism. For the purposes of this invention, the organism is a plant.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector is polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) where the expression control sequence controls and regulates the transcription and/or translation of that polynucleotide sequence.

As used herein, the term "promoter" refers to a polynucleotide that in its native state is located upstream or 5' to a translational start codon of an open reading frame (or protein-coding region) and that is involved in recognition and binding of RNA polymerase and other proteins (trans-acting transcription factors) to initiate transcription. A "plant promoter" is a native or non-native promoter that is functional in plant cells. The promoters that predominately function in particular cells and/or tissue are considered "tissue-specific promoters". A plant promoter can be used as a 5' regulatory element for modulating expression of a particular desired polynucleotide (heterologous polynucleotide) operably linked thereto. When operably linked to a transcribable polynucleotide, a promoter typically causes the transcribable polynucleotide to be transcribed in a manner that is similar to that of which the promoter is normally associated. This transcribable polynucleotide can be heterologous to the promoter, or heterologous to the organism into which the cassette will be transfected, or both. Additionally, the promoter can be heterologous to the polynucleotide.

In certain embodiments of the present invention, the expression vectors described herein contain an inducible-promoter operably linked to the polynucleotide that encodes the protein of interest. In general, inducible promoters cause a polynucleotide to be expressed under specific conditions such as, but not limited to, in specific tissue, at specific stages of development, or in response to specific environmental conditions, e.g., wounding of tissue or presence or absence of a particular compound. Inducible promoters for plants respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter can be induced by one or more of the following: abiotic stresses such as wounding, cold, desiccation, ultraviolet-B (van Der Krol, et al., *Plant Physiol.* 121:1153-1162 (1999)), heat shock (Shinmyo, et al., *Biotechnol. Bioeng.* 58:329-332 (1998)) or other heat stress, drought stress, or water stress. The promoter may further be one induced by biotic stresses, including pathogen stress, such as stress induced by a virus (Sohal, et al., *Plant Mol. Biol.* 41:75-87 (1999)) or fungi (Eulgem, et al., *Embo J.* 18:4689-4699 (1999); Cormack, et al., *Biochim Biophys Acta* 1576: 92-100 (2002)); stresses induced as part of the plant defense pathway (Lebel, et al., *Plant J.* 16:223-33 (1998)); or promoters induced by other environmental signals, such as light (Ngai, et al., *Plant J.* 12:1021-1034 (1997)), carbon dioxide (Kucho, et al., *Plant Physiol.* 121:1329-1338 (1999); Kucho, et al., *Plant Physiol.* 133:783-7893 (2003)), hormones or other signalling molecules such as auxin, hydrogen peroxide and salicylic acid (Chen, et al., *Plant J.* 19:667-677 (1999); Chen, et al., *Plant J.* 10:955-966 (1996)), sugars and gibberellin (Lu, et al., *J. Biol. Chem.* 273:10120-10131 (1998)) or abscisic acid and ethylene (Leubner-Metzger, et al., *Plant Mol. Biol.* 38:785-795 (1998)). Numerous examples may be found in Okamuro and Goldberg, *Biochemistry of Plants* 15:1-82 (1989). Rubber biosynthesis is guayule occurs place primarily in the winter, and rubber biosynthesis is cold-induced, therefore the use of a cold-inducible promoter driving expression of the Cptl gene may produce even larger increases in the amount of rubber transferase activity in the winter, when monomer metabolism and rubber storage mechanisms are not limiting. Non-limiting examples of cold-inducible promoters include cor15a and cor15b (*Arabidopsis*; Li, et al., *Plant Physiol. Biochem.*, 71:77-86 (2013) contents of which are expressly incorporated by reference), cor39 (duram wheat, Guo, et al., *Plant Physiol.*, 100:915-922 (1992) contents of which are expressly incorporated by reference), WRKY71 (rice, Kim, et al., *Plant Biotech. Rep.*, 10(1): 13-23 (2016) contents of which are expressly incorporated by reference), wcs120 (wheat, Ouellet, et al., *FEBS Letters* 423:324-328 (1998) contents of which are expressly incorporated by reference), RCI2A and RCI2B (*Arabidopsis*, Medina, et al., *Plant Physiol.* 125:1655-1666 (2001) contents of which are expressly incorporated by reference), and CBF2 (*Arabidopsis*, Zarka, et al., *Plant Physiol.*, 133:910-918 (2003) contents of which are expressly incorporated by reference).

In other embodiments of the invention, tissue-specific promoters are used in the expression vectors. Tissue-specific expression patterns are controlled by tissue- or stage-specific promoters that include, but are not limited to, fiber-specific, green tissue-specific, root-specific, stem-specific, root-specific, and flower-specific. Examples of the utilization of tissue-specific expression include, but are not limit to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable. Another example of promoters that are expressed in specific tissue are chlorophyll A/B binding protein (CAB) promoter (Bansal, et al., *Proc. Natl. Acad. Sci. USA* 89(8):3654-8 (1992)), small subunit of ribulose-1,5-bisphosphate carboxylase (ssRBCS)

promoter (Bansal, et al., *Proc. Natl. Acad. Sci. USA* 89(8): 3654-8 (1992)), phosphoenolpyruvate carboxylase 1 (PPC1) promoter (Kausch, et al., *Plant Mol. Biol.* 45(1): 1-15 (2001)), a senescence activated promoter, SEE1, (Robson, et al., *Plant Biotechnol. J.* 2(2): 101-12 (2004)), and the sorghum leaf primordia specific promoter, RS2, (GenBank Accession No. EI979305.1).

Rubber biosynthesis in guayule takes place primarily in the bark parenchyma tissues, therefore the use of a phloem-specific promoter driving the Cptl gene may be useful in producing increased levels of rubber transferase activity, thereby increasing levels of rubber production in otherwise healthy plants with high biomass. Examples of phloem-specific promoters include, but are not limited to, GRP 1.8 promoter (from French bean) (Keller and Baumgartner, (1991) *The Plcant Cell* 3:1051-1061 contents of which are expressly incorporated herein); *Arabidopsis* sucrose-$H^+$ symporter gene (AtSUC1 and AtSUC2) promoters (Sauer and Stolz (1994) *Plant J.* 6:67-77 contents of which are expressly incorporated herein); *Citrus phloem* protein 2 (CsPP2) promoter and *Arabidopsis thaliana* phloem protein 2 (AtPP2) promoter (Miyata, et al., (2012) *Plant Cell Rep.*, 31(11):2005-2013; doi 10.1007/s00299-012-1312-2 contents of which are expressly incorporated herein); and citrus phloem promoter 396s (U.S. Pat. No. 10,047,369 Belknap, et. al. contents of which are expressly incorporated herein).

In other embodiments, one can use constitutive promoters to drive expression of the polynucleotides described herein. Plant constitutive promoters are well-known in the art, and include, but are not limited to, cauliflower mosaic virus promoter (CaMV) 35S (Kay, et al. (1987) *Science* 236:1299-1302), CaMV 19S, figwort mosaic virus promoter (FMV) 35S, coat protein promoter of tobacco mosaic virus (TMV), ubiquitin promoter, opine promoter, actin 1 promoter, and alcohol dehydrogenase 1 promoter. In one embodiment, the promoter for guayule Cptl (SEQ ID NO: 18) could be considered a "heterologous promoter" because it is not naturally operably linked to a polynucleotide having a sequence of SEQ ID NOs: 1 or 2 or a sequence at least 80%, at least 85%, at least 90%, or at least 95% identical to SEQ ID NOs: 1 or 2. In another embodiment, the promoter for guayule Cptl (SEQ ID NO: 18) could not be considered a "heterologous promoter" because it is operably linked to genomic DNA that encodes a protein having an amino acid sequence of SEQ ID NO: 3. One of ordinary skill in the art will know if the guayule Cptl promoter is or is not a heterologous promoter based on the sequence of the polynucleotide to which it is operably linked. It is recognized that because, in most cases, the exact boundaries of regulatory sequences have not been completely defined, nucleic acid fragments of different lengths may have identical promoter activity.

In another embodiment, the inventions described herein use one or more of the following promoters: potato polyubiquitin promoter 409Ps (SEQ ID NO: 8), potato polyubiquitin promoter 427 (SEQ ID NO: 9) (see, also, Rockhold, et al. (2008) *Am. J. of Potato Research* 85:219-226), cold inducible promoter PCBF2 (SEQ ID NO: 10; GenBank Accession No. EF523073) (see, also, Yamaguchi-Shinozakia and Shinozakic, *Trends in Plant Sci.* 10(2): 88-94 (2005)), *Hevea brasiliensis* rubber-particle protein-specific promoter (HbSRPP, GenBank Accession No. AB861874, SEQ ID NO: 11), *H. brasiliensis* laticifer-specific promoter (HbREF, GenBank Accession No. AB861873, SEQ ID NO: 12), and *H. brasiliensis Hevea* rubber transferase 1 (HbHRT1, a.k.a. CPT1, GenBank Accession No. AB861876, SEQ ID NO: 13).

A heterologous polynucleotide sequence is operably linked to one or more transcription regulatory elements (e.g., promoter, terminator and, optionally, enhancer) such that the transcription regulatory elements control and regulate the transcription and/or translation of that heterologous polynucleotide sequence. A cassette can have the heterologous polynucleotide operably linked to one or more transcription regulatory elements. As used herein, the term "operably linked" refers to a first polynucleotide, such as a promoter, connected with a second transcribable polynucleotide, such as a gene of interest, where the polynucleotides are arranged such that the first polynucleotide affects the transcription of the second polynucleotide. In some embodiments, the two polynucleotide molecules are part of a single contiguous polynucleotide. In other embodiments, the two polynucleotides are adjacent. For example, a promoter is operably linked to a gene of interest if the promoter regulates or mediates transcription of the gene of interest in a cell. Similarly a terminator is operably linked to the polynucleotide of interest if the terminator regulates or mediates transcription of the polynucleotide of interest, and in particular, the termination of transcription. Constructs of the present invention would typically contain a promoter operably linked to a transcribable polynucleotide operably linked to a terminator.

Exemplary heterologous polynucleotide for incorporation into constructs of the present invention include, for example, desired polynucleotides from a species other than the target plant's species, or even desired polynucleotides that originate with or are present in the same plant species, but are incorporated into the genetically altered plant cells by genetic engineering methods rather than classical reproduction or breeding techniques or by a combination of genetic engineering methods followed by breeding techniques. Heterologous polynucleotides refer to any polynucleotide molecule that is introduced into a recipient cell and is transcribed at levels that differ from the wild-type cell. A heterologous polynucleotide can include a polynucleotide that is already present in the plant cell, polynucleotide from another plant, polynucleotide from a different organism, or a polynucleotide generated externally, such as a polynucleotide containing an anti-sense message of a gene, or a polynucleotide encoding an artificial or modified version of a gene.

Transformation and generation of genetically altered monocotyledonous and dicotyledonous plant cells is well known in the art. See, e.g., Weising, et al., *Ann. Rev. Genet.* 22:421-477 (1988); U.S. Pat. No. 5,679,558 (herein incorporated by reference in its entirety); *Agrobacterium* Protocols. ed: Gartland, Humana Press Inc. (1995); and Wang, et al. *Acta Hort.* 461:401-408 (1998). One transformation technique used to generate genetically altered guayule is described in Dong, et al. (2006) *Plant Cell Rep.* 25:26-34. A method to generate genetically altered guayule is described in U.S. Pat. No. 9,018,449 (Dong & Cornish) (herein incorporated by reference). A method to generate transplastomic guayule is provided in U.S. Patent Application Publication 2014/0325699 (herein incorporated by reference in its entirety). One may choose a transformation method that suits the type of plant to be transformed, the particular application, and/or the desired result. The appropriate transformation technique is readily chosen by the skilled practitioner.

Exemplary transformation/transfection methods available to those skilled in the art include, but are not limited to: direct uptake of foreign DNA constructs (see, e.g., EP 295959); techniques of electroporation (see, e.g., Fromm et al., *Nature* 319:791 (1986)); and high-velocity ballistic bombardment with metal particles coated with the nucleic acid constructs (see, e.g., Kline, et al., *Nature* 327:70 (1987) and U.S. Pat. No. 4,945,050 (herein incorporated by reference in its entirety)). Specific methods to transform heterologous genes into commercially important crops (to make genetically altered plants) are published for rapeseed (De Block, et al., *Plant Physiol.* 91:694-701 (1989)); sunflower (Everett, et al., *Bio/Technology* 5:1201 (1987)); soybean (McCabe, et al., *Bio/Technology* 6:923 (1988), Hinchee, et al., *Bio/Technology* 6:915 (1988), Chee, et al., *Plant Physiol.* 91:1212-1218 (1989), and Christou, et al., *Proc. Natl. Acad. Sci USA* 86:7500-7504 (1989)); rice (Hiei, et al., *Plant J.* 6:271-282 (1994)), and corn (Gordon-Kamm, et al., *Plant Cell* 2:603-618 (1990), and Fromm, et al., *Biotechnology* 8:833-839 (1990)). Other known methods are disclosed in U.S. Pat. Nos. 5,597,945; 5,589,615; 5,750,871; 5,268,526; 5,262,316; and 5,569,831 (all herein incorporated by reference in their entirety).

One exemplary method includes employing *Agrobacterium tumefaciens* or *Agrobacterium rhizogenes* as the transforming agent to transfer heterologous DNA into the plant. *Agrobacterium tumefaciens*-meditated transformation techniques are well described in the scientific literature. See, e.g., Horsch, et al. *Science* 233:496-498 (1984), and Fraley, et al. *Proc. Natl. Acad. Sci. USA* 80:4803 (1983). Typically, a plant cell, an explant, a meristem or a seed is infected with *Agrobacterium tumefaciens* transformed with the expression vector/construct which contains the heterologous nucleic acid operably linked to a promoter. Under appropriate conditions known in the art, the transformed plant cells are grown to form shoots, roots, and develop further into genetically altered plants. In some embodiments, the heterologous nucleic acid can be introduced into plant cells, by means of the Ti plasmid of *Agrobacterium tumefaciens*. The Ti plasmid is transmitted to plant cells upon infection by *Agrobacterium tumefaciens*, and is stably integrated into the plant genome. See, e.g., Horsch, et al. (1984), and Fraley, et al. (1983).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture*, in *Handbook of Plant Cell Culture*, pp. 124-176, MacMillan Publishing Company, New York, 1983; and Binding, *Regeneration of Plants*, in *Plant Protoplasts*, pp. 21-73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467-486 (1987). Methods for generating genetically altered guayule can be found in U.S. Patent App. Pub. 2014/0325699 and in U.S. patent application Ser. No. 14/075,761 filed Nov. 8, 2013 (all herein incorporated by reference in their entirety).

Once a genetically altered diploid plant has been generated, one can breed it with a wild-type plant and screen for heterozygous F1 generation diploid plants containing the genetic change present in the parent genetically altered plant. Then F2 generation diploid plants can be generated which are homozygous for the genetic alteration for diploid species. These heterozygous F1 generation plants and homozygous F2 plants, progeny of the original genetically altered plant, are considered genetically altered plants, having the altered genomic material from the genetically altered parent plant.

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology*, 1994—current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The term "plant" includes whole plants, plant organs, progeny of whole plants or plant organs, embryos, somatic embryos, embryo-like structures, protocorms, protocorm-like bodies (PLBs), and suspensions of plant cells. A part of a plant can be a plant's organs such as shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary). Plant tissue (e.g., vascular tissue, ground tissue, and the like) and cells (e.g., any cell from the plant, guard cells, egg cells, trichomes and the like) are also considered a part of a plant in one embodiment. The various compounds produced by a plant are part of the plant, and, in particular, the rubber produced by guayule is part of the guayule. The class of plants that can be used in the method of the invention is generally as broad as the class of higher and lower plants amenable to the molecular biology and plant breeding techniques described herein, specifically angiosperms (monocotyledonous (monocots) and dicotyledonous (dicots) plants). It includes plants of a variety of ploidy levels, including aneuploid, polyploid, diploid, haploid and hemizygous.

In one embodiment, guayule are transiently transfected by direct injection into the stem, or by spraying a suspension of *A. tumefaciens* containing the expression vector necessary to induce silencing onto the guayule's leaves. Transiently transfected plants are subsequently rinsed to wash away the delivery agent (*A. tumefaciens*), and transplanted to the field. Unlike traditional biotechnology approaches, such treated plants are not permanently genetically altered. Direct injection can be performed by the protocol set forth in Ryu, et al., *Plant J.* 40:322-331 (2004). Spraying guayule with *A. tumefaciens* can be performed by the protocol set forth in Dinesh-Kumar, Cold Spring Harbor protocol 2009.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1. Obtaining Guayule Cptl cDNA Sequence

Using computer software that compares sequences (BLAST®), searches of the guayule genome assemblies, genomic reads (100× coverage) or the transcriptome (>400× coverage) employing lettuce Cptl2 protein sequence (SEQ ID NO: 4) and dandelion TbRta protein sequence (SEQ ID NO: 5) indicate a single guayule genomic locus with significant similarity (E value<1e−15) to the lettuce and dandelion proteins.

Based on the sequence information obtained from the sequence comparison, the following RT-PCR forward/reverse primers are designed to amplify full-length guayule Cptl:

```
RT-PCR forward primer
                              (SEQ ID NO: 14)
5'-TCAAGATACCACTCTACTATGGATCTAGT-3'
and RT-PCR reverse primer
                              (SEQ ID NO: 15)
5'-ATTTTGCTCCCCTTGAGTC-3',
```

1 µg of AZ2 guayule RNA is used for RT-PCR using Qiagen OneStep RT-PCR Kit (Qiagen, Germantown, Md.) following manufacturer's recommended protocol: reverse transcription: 30 minutes, 50° C.; initial PCR activation: 15 minutes, 95° C.; 3-step PCR 30 cycles: 0.5 minute, 95° C., 1 minute, 55° C., 1 minute, 72° C.; and final extension: 10 minutes, 72° C. 0.6 µM each of RT-PCR forward primer (SEQ ID NO: 14) and RT-PCR reverse primer (SEQ ID NO: 15) are added to the RT-PCR reaction mixture. To verify that a single PCR amplicon is produced, the DNA is run on an agrose gel, and an amplicon of ~816 bp is observed. This amplicon is excised from the gel, purified use QIAquick® Gel Extraction Kit (Qiagen, Germantown, Md.) and is cloned into pCR4 vector of TOPO TA Cloning Kit (Invitrogen, Carlsbad, Calif.) following manufacturer's recommended protocol: mix gently 4 µl (275 ng) of DNA and 1 µl of TOPO pCR4 vector, incubate for 5 minutes at room temperature, place reaction tube on ice, and proceed with *E. coli* transformation. The obtained plasmid is sequenced to verify the sequence of Cptl. The sequence of Cptl cDNA is in SEQ ID NO: 1.

Example 2. Cptl Expression Analysis in Field-Grown Guayule

Field-grown guayule (wild-type) are harvested on the dates indicated in FIG. 5. Two µg of total RNA are extracted from the harvested guayule stem bark tissue and is used as template for cDNAs using the SuperScript™ III First-Strand Synthesis System for Reverse Transcriptase (RT)-PCR (ThermoFischer Scientific, Waltham, Mass.). Quantitative PCR (qPCR) on cDNAs of Cptl and Eif4A (endogenous control gene) is carried out using Applied Biosystems™ 7500 Fast Real Time PCR System and the SYBR® Green (green fluorescence dye) chemistry (ThermoFischer Scientific, Waltham, Mass.). To calculate mean relative expression levels, cDNAs are analyzed in triplicate in the same 96-well micro chamber plate. Gene primer efficiencies and relative expression ratios are calculated according to methods described in Pfaffl, M., *Nucleic Acids Res.* 29(9):e45 (May 1, 2001). Efficiencies are 2.11 for Cptl and 1.99 for Eif4A. Expression of Ctpl target gene as normalized to expression of the constitutively expressed endogenous reference gene Eif4A, and then to its expression in a calibrator (guayule plant grown in warm temperature [June 2006]). The following combinations of forward/reverse primers are used for the qPCR reactions: for Cptl, 5'-GGCGGTCATCATG-GAGAGA-3' (forward primer (SEQ ID NO: 19)) and 5'-GATTGGCTACTGCACTATCATTGG-3' (reverse primer (SEQ ID NO: 20)); for Eif4A 5'-TT-GAATGCCAGGCTTTGGTT-3' (forward primer (SEQ ID NO: 21)); 5'-GCGCGCATGACCTTCTCA-3' (reverse primer (SEQ ID NO: 22)). Fast SYBR® Green (green fluorescence dye) Master Mix (2X) is used in each qPCR reaction with 200 ng cDNA in combination with 300 nM each primer. Thermocycler temperature regime: 95° C. for 20 seconds, followed by 40 cycles of 95° C. for 3 seconds and 60° C. for 30 seconds. Data (FIG. 5) are analyzed using the Applied Biosystems™ 7500 Fast System Detection Software (ThermoFischer Scientific, Waltham, Mass.) with manually set baseline and threshold.

Highest rubber synthesis in guayule occurs during the coldest months of the year. As seen in FIG. 5, the highest expression of PaCptl occurs in plants harvested in November 2005, February 2006, October 2006, December 2006, and January 2007, indicating that PaCptl expression is cold induced. While, the data is not perfect because PaCptl expression in guayule harvested in December 2005 and November 2006 is extremely low, these outlying expression data may be attributed to sampling error and/or the temperature on the actual harvest day. This correlation between higher PaCptl expression and cold temperature supports the view that Cptl is an important protein for rubber synthesis. Further, cold induction of rubber synthesis in guayule probably is caused by the cold-inducibility of PaCptl. Thus, overexpression of PaCptl (in cold or warm or both temperatures) in genetically altered guayule should increase rubber production in the genetically altered guayule compared to the amount of rubber produced by wild-type guayule (in cold or warm or both temperatures).

Example 3. Maintenance of Guayule Plants In-Vitro

Guayule line G7-11 is established as described previously (see, Castillon and Cornish (2000) *In Vitro Cell Dev. Biol.-Plant* 36(3):215-219). A shoot tip 10 mm or longer is excised and is transferred to a Magenta box containing 80 ml fresh ½ MS-I0.1 [half-strength MS medium (Murashige and Skoog (1962) *Physiol. Plant* 15:473-479) plus 2.5 mM $CaCl_2$, 2.0 mM $Mg(NO_3)_2$, 0.1 mg/l indole-3-butyric acid (IBA), 15 g/l sucrose and 3.2 g/l Phytagel™ (item P8169, Sigma-Aldrich, St. Louis, Mo.), pH 5.8. MS vitamin is replaced with B5 vitamin (Gamborg, et al. (1968) *Exp. Cell Res.* 50:151-158). The cultures are maintained at 25° C. under cool-white fluorescent light (~50 µmol/m²/s, 16/8-hour day/night photoperiod). Roots develop 1-2 weeks after the shoot tips are transferred to this medium. Each shoot tip is transferred to new medium every 2 months.

Example 4. Plasmid Construction and *Agrobacterium* Preparation

Plasmid pND9 (control vector) is constructed based on pPZP200 (Hajdukiewicz, et al. (1994) *Plant Mol. Biol.* 25:989-994). It contains a potato polyubiquitin promoter 409Ps (Garbarino, et al. (1995) *Plant Phys.* 109:1371-1378) (SEQ ID NO: 8) operably linked to Nptii gene (Beck, et al. (1982) *Gene* 19:327-336) and a double CaMV 35S promoter operably linked to GUSplus gene (provided by CAMBIA). Plasmid pND9-409P-CPTL is constructed by replacing the GUSplus gene with the Cptl gene, operably linked to potato polyubiquitin promoter 409P. Of course, other promoters, such as the ones discussed above could be used. Plasmid pND9-409P-CPTL is used to transform *Agrobacterium* EHA101 (Hood, et al. (1986) *J. Bacteriol.* 168:1291-1301) competent cells. The transformed *Agrobacterium* EHA101 harboring pND9-409P-CPTL is used to transform the guayule G7-11 leaf tissue.

*Agrobacterium* overnight culture is prepared by inoculating 50 µl long-term glycerol stock into a 50 ml Falcon tube containing 5 ml LB medium plus 20 mg/l rifampicin and 200 mg/l spectinomycin, and shaking at 200 rpm at 28° C. The suspension then is centrifuged for 15 minutes at 1,600×g at room temperature. The supernatant is discarded, and the pellet is re-suspended in 25 ml of Inoculation Solution (1/10 MS salts plus 1 mg/l boric acid (BA), 0.25 mg/l 1-naphthaleneacetic acid (NAA), 10 g glucose, 200 µM acetosyringone, 0.05% Pluronic F68, at pH 5.2).

Example 5. Leaf Tissue Transformation

The leaf tissue transformation protocol set forth in Dong, et al. (2006) *Plant Cell Rep.* 25:26-34 is followed with some modifications. Leaves are cut from the plants in the Magenta boxes. Each leaf is placed in a Petri dish containing 5 ml *Agrobacterium* suspension. The adaxial side (upper side) is up. The leaf is cut into 10 mm strips and around 17 leaf strips are transferred to an empty Petri dish. All leaf strips are blotted with the filter paper and are placed in an empty Petri dish without overlap. The Petri dish is sealed by parafilm and left in dark. The co-cultivation is replaced by this co-desiccation using the protocol set forth in Cheng, et al. (2003) *In Vitro Cell. Dev. Biol. Plant* 39:595-604 such that the leaf tissue are drying in the presence of *Agrobacterium*. Three days later, leaf strips are transferred to MSB1T (MS Modified Basal Medium (item M541, PhytoTechnology Laboratories (Shawnee Mission, Kans.)), plus 1 mg/l BA, 0.25 mg/l NAA, 30 g/l sucrose, 3.2 g/l Phytagel™ (item P8169, Sigma-Aldrich, St. Louis, Mo.), and 400 mg/l timentin for recovery at low light for 5 days. See, Cheng, et al. (1998) *Plant Cell Rep.* 17(8):646-649.

The leaf strips are then transferred to MSB0.75TK30 (which is similar to MSB1T but containing 0.75 mg/l BA and 30 mg/l kanamycin) for selection under low light. Two weeks later, the leaf strips are transferred to the same medium and are subcultured every 2 weeks under high light until green shoots emerged. Green shoots 10 mm and longer are transferred to ½ MSI0.1TK10 (same as ½ MSI0.1 but containing 200 mg/l timentin and 10 mg/l kanamycin) for rooting for 2-4 weeks. Shoot tips of the rooted plantlets are transferred to ½ MSI0.1 for maintenance or are inserted into a sterile cellulose plug in liquid ½ MSI0.1 medium for rooting and then are transplanted into soil.

PCR analysis is then performed on the genetically altered guayule shoots. DNA is extracted using GenElute™ Plant Genomic DNA Miniprep Kit (Sigma-Aldrich, St. Louis, Mo.) following manufacturer's recommended protocol. Approximately 150 mg leaf tissue is frozen in liquid nitrogen and ground to a fine powder using a mortar and pestle. PCR is carried out in 50 µl of a mixture containing 5 units of Taq DNA polymerase (New England Biolabs, Ipswich, Mass.) and 5 µl of 10×ThermoPol® Reaction Buffer (New England Biolabs, Ipswich, Mass.), 4 µl of dNTP (2.5 mM each), 200 ng genomic DNA, and 0.8 µM of CPTL specific PCR forward and PCR reverse primers (PCR forward primer: 5'-ATGGAAGTCAATCCAATCATC-3' (SEQ ID NO: 16) and PCR reverse primer: 5'-GAAGAAGAAGCAGGCTTGA-3'(SEQ ID NO: 17)). After heating the samples to 94° C. for 2 minutes, the reaction proceeds with 35 cycles of 94° C. for 30 seconds, 55° C. for 30 seconds, and 72° C. for 30 seconds. A final elongation step is carried out at 72° C. for 10 minutes. PCR products are separated by electrophoresis on 0.9% (w/v) agarose gels.

Example 6. Determination of Rubber Content for Genetically Altered Tissue-Culture Plants Overexpressing Cptl Rooted plantlets from transferred shoot tips are grown on ½ MSI0.1 medium in Magenta boxes. The plantlets are placed in a Conviron CMP5090 growth chamber (Winnipeg, Canada) under 25° C. 16 hour day/10° C. 8 hour nights for at least 90 days. At approximately 30, approximately 60, and approximately 90 days post-shoot-tip transfer, some plantlets are carefully separated from the medium and lyophilized for 48-72 hours. The dried tissues are cryoground in a Retsch ball mill/stainless steel cell for 30 seconds at 35 rpm. A weighed aliquot (approximately 200 mg) of ground tissue is then partitioned with sand and loaded into 11 mL stainless steel cells for extraction by Accelerate Solvent Extraction (Dionex Corp., Sunnyvale, Calif.) using manufacturer's recommended protocol. Three sequential extractions are performed at ambient temperature in acetone, to remove and quantify the level of resinous material and the low molecular weight organic solubles, next with methanol, to remove chlorophyll and other alcohol-soluble materials (following protocol set forth in Pearson et al. (2010) *Industrial Crops and Products* 31: 469-475) and finally with cyclohexane, to extract and quantify the natural rubber content. Natural rubber is quantified gravimetrically from the weight of ASE vial cyclohexane extracts and confirmed by NMR. The amount of rubber produced by the genetically altered guayule is more than the amount of rubber produced by the wild-type guayule.

Example 7. Measuring Guayule Cptl mRNA Levels to Distinguish Between Genetically Altered Guayule Containing Heterologous Promoter Operably Linked to Guayule Cptl and Wild-Type Guayule One can distinguish between genetically altered guayule containing a heterologous promoter operably linked to guayule Cptl and wild-type guayule that do not contain extra copies of guayule Cptl by measuring Cptl mRNA levels using quantitative real time PCR (qRT-PCR). Leaf tissue from tissue culture guayule is the source of total RNA template (1 µg) for cDNA synthesis using the iScript cDNA Synthesis kit (Bio Rad, Hercules, Calif.) following manufacturer's recommended protocol. qRT-PCR on cDNAs of Cpt1 and Eif4a (endogenous guayule control gene) is carried out using Applied Biosystems™ 7500 Fast Real Time PCR System (ThermoFischer Scientific, Waltham, Mass.) and Fast SYBR® Green (green fluorescence dye) Master Mix (ThermoFischer Scientific, Waltham, Mass.) with the following combination of forward and reverse primers (300 μM each): for Cpt1, 5'-GGCGGTCATCATGGAGAGA-3' (forward primer (SEQ ID NO: 19)) and 5'-GATTGGC-TACTGCACTATCATTGG-3' (reverse primer (SEQ ID NO: 20)); for Eif4a, 5'-TTGAATGCCAGGCTTTGGTT-3' (forward primer (SEQ ID NO: 21)) and 5'-GCGCG-CATGACCTTCTCA-3' (reverse primer (SEQ ID NO: 22)). Temperature regime: 95° C. for 20 seconds, followed by 40 cycles of 95° C. for 3 seconds and 60° C. for 30 seconds. Data is analyzed with the 7500 Fast System Detection Software (Applied Biosystems™; ThermoFischer Scientific, Waltham, Mass.) with manually set baseline and threshold.

Example 8. Rubber Transferase (RuT) Activity Quantification

With the increased amount of Cpt1 being produced by the genetically altered guayule, an increase amount of rubber transferase (RuT) activity occurs. To measure RuT activity, first one needs to prepare enzymatically-active rubber particles using the following protocol. Mature *P. argentatum* shrubs are freshly harvested, stored at 4° C., and processed within 96 hours. Bark tissue from stems is homogenized, and rubber particles isolated and purified using the methods described in Siler and Cornish (1993) *Phytochemistry* 32, 1097-1102 and in Cornish and Backhaus (1990) *Phytochemistry* 29, 3809-3813.

Next, in-vitro quantification of rubber transferase activity is quantified by determining isopentenyl pyrophosphate (IPP) incorporation rates using a modification of a previously described method (Mau, et al., (2000) *Phytochem. Anal.* 11:356-361). The reaction takes place in the wells of 96-well filter plate, or in an eppendorf tube. For the 96-well plate, the reaction volume was 40 μl containing 100 mM Tris-HCl, pH 7.5, 1.25 mM $MgSO_4$, 5 mM DTT, 1 mM unlabelled IPP, and 0.9 nmol [$^{14}C$]IPP. Each well also contains 0.5 mg washed rubber particles (WRPs). The reaction time is 4 hours at 16° C. for *P. argentatum* (Cornish and Backhaus, 1990). Reactions are then stopped by addition of 40 mM EDTA. The filter plate is washed twice with 150 μl water and twice with 95% ethanol, then oven-dried at 37° C. for 30 mins. The filters are removed from the plate and placed into vials with 1.5 ml ScintVerse BD Cocktail. The amount of [$^{14}C$] IPP incorporated into newly synthesized rubber is determined by scintillation counting (Beckman Coulter, Fullerton, Calif., USA), and corresponds to rubber transferase activity.

Further, when one compares the amount of Cpt1 mRNA present in a genetically altered guayule to the amount of rubber produced by that genetically altered guayule, one notes that the mRNA levels are elevated for those genetically altered guayule that produce elevated levels of rubber, compared to the mRNA levels and amount of rubber produced by wild-type guayule. In addition, the genetically altered guayule that overexpress Cpt1 produce increased amount of Cpt1 and produce increased amount of rubber compared to the amount of Cpt1 and rubber produced by wild-type guayule.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim as follows:

1. An expression vector comprising a heterologous promoter operably linked to a cDNA comprising SEQ ID NO: 2 or a sequence at least 90% identity to SEQ ID NO: 2, wherein said cDNA encodes a protein capable of activating cis-prenyltransferase (Cpt) and wherein said protein comprises an amino acid sequence with at least 90% identity to SEQ ID NO: 3.

2. The expression vector of claim 1, wherein said heterologous promoter is a tissue-specific promoter or a cold-inducible promoter.

3. The expression vector of claim 2, wherein said tissue-specific promoter is a phloem specific promoter.

4. The expression vector of claim 3, wherein said phloem specific promoter is selected from the group consisting of Glycine-rich cell wall protein (GRP) 1.8 promoter, Arabidopsis thaliana sucrose transport 1 (AtSUC1) promoter, Arabidopsis thaliana sucrose transport 2 (AtSUC2) promoter, citrus phloem protein 2 (CsPP2) promoter, Arabidopsis thaliana phloem protein (AtPP2) promoter, and citrus phloem small cyclic amphipathic protein promoter 396SS.

5. The expression vector of claim 2, wherein said cold-inducible promoter is selected from the group consisting of cold regulated 15a (Cor15a), cold regulated 39 (Cor39), WRKY71, wheat cold specific 120 (Wcs120), rare cold inducible 2A/2B (RCI2A/RCI2B), and C-repeat binding factor 2 (CBF2).

6. A transformed cell comprising the expression vector of claim 1.

7. The transformed cell of claim 6, wherein said transformed cell is a transformed plant cell, a transformed bacterial cell, or a transformed fungus cell.

8. The transformed plant cell of claim 7, wherein said transformed plant cell is a transformed guayule cell.

9. An expression vector comprising a heterologous promoter operably linked to a polynucleotide encoding the amino acid sequence of SEQ ID NO: 3 or a sequence at least 90% identical to SEQ ID NO: 3, wherein said amino acid sequence is capable of activating cis-prenyltransferase (Cpt).

10. The expression vector of claim 9, wherein said heterologous promoter is a tissue-specific promoter or a cold-inducible promoter.

11. The expression vector of claim 10, wherein said tissue-specific promoter is a phloem specific promoter.

12. The expression vector of claim 11, wherein said phloem specific promoter is selected from the group consisting of GRP 1.8 promoter, AtSUC1 promoter, AtSUC2 promoter, CsPP2 promoter, AtPP2 promoter, and citrus phloem promoter 396SS.

13. The expression vector of claim 10, wherein said cold-inducible promoter is selected from the group consisting of cor15a, cor39, WRKY71, wcs120, RCI2A, RCI2B, and CBF2.

14. A transformed cell comprising the expression vector of claim 9.

15. The transformed cell of claim 13, wherein said transformed cell is a transformed plant cell, a transformed fungus cell, or a transformed bacterial cell.

16. The transformed plant cell of claim 15, wherein said transformed plant cell is a transformed guayule cell.

17. A genetically altered guayule comprising said expression vector of claim 1 that produces an increased amount of rubber compared to the amount of rubber produced by a control wild-type guayule,
   wherein said genetically altered guayule produces an increased amount of cis-prenyltransferase-like (Cptl) protein compared to an amount of Cptl protein produced by said wild-type guayule, and
   wherein said increased amount of said Cptl protein causes said genetically altered guayule to produce said increased amount of rubber compared to said amount of rubber produced by said wild-type guayule.

18. A germplasm of said genetically altered guayule of claim 17.

19. A genetically altered seed of said genetically altered guayule of claim 17, wherein said genetically altered seed comprises an expression vector comprising a heterologous promoter operably linked to a cDNA comprising SEQ ID NO: 2 or a sequence at least 90% identical to SEQ ID NO: 2.

20. A genetically altered guayule comprising said expression vector of claim 9 that produces an increased amount of rubber compared to the amount of rubber produced by a control wild-type guayule,
   wherein said genetically altered guayule produces an increased amount of Cptl protein compared to an amount of Cptl protein produced by said wild-type guayule, and
   wherein said increased amount of said Cptl protein causes said genetically altered guayule to produce said increased amount of rubber compared to said amount of rubber produced by said wild-type guayule.

21. A germplasm of said genetically altered guayule of claim 20.

22. A genetically altered seed of said genetically altered guayule of claim 20, wherein said genetically altered seed comprises an expression vector comprising a heterologous promoter operably linked to a polynucleotide encoding a Cptl protein comprising the sequence of SEQ ID NO: 3 or a sequence at least 90% identical to SEQ ID NO: 3.

23. A method of increasing an amount of rubber produced by a genetically altered guayule compared to the amount of rubber produced by a control wild-type guayule, the method comprising:
   (a) transforming a wild-type guayule cell with an expression vector to produce a transformed guayule cell; wherein said expression vector comprises a heterologous promoter operably linked to a polynucleotide encoding a Cptl protein comprising the amino acid sequence of SEQ ID NO: 3 or a sequence at least 90% identical to SEQ ID NO: 3;

(b) selecting said transformed guayule cell that produces an increased amount of said Cptl protein compared to an amount of said Cptl protein produced by said wild-type guayule to provide a genetically altered guayule cell; and (c) growing said genetically altered guayule cell into a genetically altered guayule, wherein said genetically altered guayule produces said increased amount of said Cptl protein compared to said amount of said Cptl protein produced by said wild-type guayule, and wherein said increased amount of said Cptl protein causes said genetically altered guayule to produce said increased amount of rubber compared to said amount of rubber produced by said wild-type guayule.

24. The method of claim 23, wherein said polynucleotide comprises a sequence selected from the group consisting of SEQ ID NO: 1, a sequence at least 90% identical to SEQ ID NO: 1, SEQ ID NO: 2, and a sequence at least 90% identical to SEQ ID NO: 2.

25. A genetically altered guayule or part thereof produced by the method of claim 23.

26. A genetically altered germplasm of the genetically altered guayule of claim 25.

* * * * *

SEQUENCE LISTING

<160> NUMBER OF SEQ ID NOS: 22

<210> SEQ ID NO 1
<211> LENGTH: 971
<212> TYPE: DNA
<213> ORGANISM: Parthenium argentatum

<400> SEQUENCE: 1

```
ttaacttaac ctcctctatt tcaatccatc atctattgga ttcaagcatc acagatcaag      60
ataccactct actatggatc tagtagctga atcacagaag tttttttcgca ggacctcgca     120 gagtggcagc attgtgctct tcttgctctg gcatgtagtt cacttaacaa tcagtgtttt     180
atacattgtc cgggagatct ttcgtgcgat tgaaagctac cttataacaa acggatatgt     240
gaaaacatac acaaatataa atttacaacg ggtcaaatat cttggaattg ttgtggacag     300
tgatgaagcc cgtaacatct caaaagtggt tgaacttta gagtggcttt cagctatagg     360
tgtgaaaaag atctgtcttt atgaccggga aggagtgttg aagaagtcaa aggcggtcat     420
catggagaga tttggctcta cagagacttc caatgatagt gcagtagcca atccactaag     480
taaaaaacgg atggattttg aatttgtttc aatcactgat ggcaaagaag cagttgctaa     540
agcagctaac ctactctta aaaaatatta tgtggacgaa gaatcagaaa aaccattctt     600
tactgaaacc cacttgaccg aggcactaaa gaccctcggg caagtagagc cagatcccga     660
```

```
tcttttatta atttacgggc cagtgaggtg ccaccttggt tttccagcat ggcgacttcg    720
ttacacggag atggtgcaca tgggaccatt aaagtacaag aaatttggtt tgattctgaa    780
agcaattcac aggttcacta aggtgaagca aaactatggt tcataagatt ctagtactca    840
ggactagttg atgactcaag gggagcaaaa taccaagtga agggtcctta atgaagtgag    900
caattcagat gcatttgtgg ttgtgtggtt gtttatatct gtattttgaa atcaataagt    960
aatcttgctt t                                                          971

<210> SEQ ID NO 2
<211> LENGTH: 753
<212> TYPE: DNA
<213> ORGANISM: Parthenium argentatum

<400> SEQUENCE: 2
atggatctag tagctgaatc acagaagttt tttcgcagga cctcgcagag tggcagcatt     60
gtgctcttct tgctctggca tgtagttcac ttaacaatca gtgttttata cattgtccgg    120
gagatctttc gtgcgattga agctacccct ataacaaacg gatatgtgaa acatacaca    180 aatataaatt tacaacgggt caaatatctt ggaattgttg tggacagtga tgaagcccgt    240
aacatctcaa aagtggttga acttttagag tggctttcag ctataggtgt gaaaaagatc    300
tgtctttatg accgggaagg agtgttgaag aagtcaaagg cggtcatcat ggagagattt    360
ggctctacag agacttccaa tgatagtgca gtagccaatc cactaagtaa aaaacggatg    420
gattttgaat tgtttcaat cactgatggc aaagaagcag ttgctaaagc agctaaccta    480
ctctttaaaa aatattatgt ggacgaagat tcagaaaaac cattctttac tgaaacccac    540
ttgaccgagg cactaaagac cctcgggcaa gtagagccag atcccgatct tttattaatt    600
tacgggccag tgaggtgcca ccttggtttt ccagcatggc gacttcgtta cacggagatg    660
gtgcacatgg gaccattaaa gtacaagaaa tttggtttga ttctgaaagc aattcacagg    720
ttcactaagg tgaagcaaaa ctatggttca taa                                 753

<210> SEQ ID NO 3
<211> LENGTH: 250
<212> TYPE: PRT
<213> ORGANISM: Parthenium argentatum

<400> SEQUENCE: 3

Met Asp Leu Val Ala Glu Ser Gln Lys Phe Phe Arg Arg Thr Ser Gln
1               5                   10                  15

Ser Gly Ser Ile Val Leu Phe Leu Leu Trp His Val Val His Leu Thr
            20                  25                  30

Ile Ser Val Leu Tyr Ile Val Arg Glu Ile Phe Arg Ala Ile Glu Ser
        35                  40                  45

Tyr Leu Ile Thr Asn Gly Tyr Val Lys Thr Tyr Thr Asn Ile Asn Leu
    50                  55                  60

Gln Arg Val Lys Tyr Leu Gly Ile Val Val Asp Ser Asp Glu Ala Arg
65                  70                  75                  80

Asn Ile Ser Lys Val Val Glu Leu Leu Glu Trp Leu Ser Ala Ile Gly
                85                  90                  95

Val Lys Lys Ile Cys Leu Tyr Asp Arg Glu Gly Val Leu Lys Lys Ser
            100                 105                 110

Lys Ala Val Ile Met Glu Arg Phe Gly Ser Thr Glu Thr Ser Asn Asp
        115                 120                 125
```

```
Ser Ala Val Ala Asn Pro Leu Ser Lys Lys Arg Met Asp Phe Glu Phe
    130                 135                 140

Val Ser Ile Thr Asp Gly Lys Glu Ala Val Ala Lys Ala Ala Asn Leu
145                 150                 155                 160

Leu Phe Lys Lys Tyr Tyr Val Asp Glu Asp Ser Glu Lys Pro Phe Phe
                165                 170                 175

Thr Glu Thr His Leu Thr Glu Ala Leu Lys Thr Leu Gly Gln Val Glu
                180                 185                 190

Pro Asp Pro Asp Leu Leu Leu Ile Tyr Gly Pro Val Arg Cys His Leu
                195                 200                 205

Gly Phe Pro Ala Trp Arg Leu Arg Tyr Thr Glu Met Val His Met Gly
210                 215                 220

Pro Leu Lys Tyr Lys Lys Phe Gly Leu Ile Leu Lys Ala Ile His Arg
225                 230                 235                 240

Phe Thr Lys Val Lys Gln Asn Tyr Gly Ser
                245                 250

<210> SEQ ID NO 4
<211> LENGTH: 244
<212> TYPE: PRT
<213> ORGANISM: Lactuca sativa

<400> SEQUENCE: 4

Met Asp Leu Val Gly Gly Pro Gln Lys Ile Leu His Lys Ile Ser Leu
1               5                   10                  15

Asn Asp His Met Ile Leu Leu Leu Trp His Ile Leu His Leu Ile
                20                  25                  30

Val Gln Val Ile Tyr Phe Val Trp Glu Lys Met Arg Ala Ile Glu Ser
                35                  40                  45

Tyr Leu Ile Ala Asn Gly Ile Val Lys Thr Tyr Glu Asp Leu Asn Leu
            50                  55                  60

Asp Arg Val Lys Tyr Leu Gly Ile Val Val Asp Ser Asp Glu Ala Arg
65                  70                  75                  80

Glu Thr Ser Lys Val Ile Glu Leu Leu Glu Trp Ile Ser Asp Ile Gly
                85                  90                  95

Val Lys Lys Val Cys Leu Tyr Asp Arg Glu Gly Val Leu Lys Lys Ser
                100                 105                 110

Lys Glu Leu Phe Met Glu Lys Phe Asp Ser Met Glu Asn Ser Glu Thr
            115                 120                 125

Asn Gln Lys Arg Lys Met Asp Phe Glu Phe Val Ser Ile Val Asp Gly
130                 135                 140

Lys Glu Thr Val Ala Lys Ala Ala Asn Leu Leu Tyr Lys Lys Tyr Tyr
145                 150                 155                 160

Ser Asp Pro Asn Ser Glu Lys Pro Phe Phe Thr Glu Thr Tyr Leu Thr
                165                 170                 175

Glu Ala Leu Arg Ile Leu Gly Ser Asn Glu Pro Asp Pro Asp Leu Ile
            180                 185                 190

Leu Ile Tyr Gly Pro Thr Arg Cys His Leu Gly Phe Pro Ala Trp Arg
            195                 200                 205

Ile Arg Tyr Thr Glu Met Val His Met Gly Ser Leu Lys Asn Lys Lys
210                 215                 220

Phe Gly Leu Ile Leu Lys Ala Ile Asn Lys Tyr Thr Lys Val Lys Gln
225                 230                 235                 240

Asn Tyr Gly Ser
```

<210> SEQ ID NO 5
<211> LENGTH: 244
<212> TYPE: PRT
<213> ORGANISM: Taraxacum brevicorniculatum

<400> SEQUENCE: 5

```
Met Asp Leu Leu Asp Gly Pro Gln Lys Ile Tyr Arg Lys Ile Ser Gln
1               5                   10                  15
Asn Glu Asn Ile Val Leu Leu Leu Trp His Val Leu His Leu Ile
            20                  25                  30
Ile Lys Phe Met Tyr Phe Val Arg Glu Ile Leu Arg Gly Ile Glu Asn
                35                  40                  45
Tyr Leu Ile Ile Asn Glu Ile Val Lys Thr Tyr Glu Asp Leu Asn Leu
        50                  55                  60
Asn Arg Val Lys Tyr Leu Gly Ile Val Val Asp Ser Asp Glu Ala Arg
65                  70                  75                  80
Glu Thr Ser Lys Val Ile Glu Leu Leu Glu Trp Leu Ser Asp Ile Gly
                85                  90                  95
Val Lys Lys Val Cys Leu Tyr Asp Arg Glu Gly Val Leu Lys Lys Ser
            100                 105                 110
Lys Glu Val Phe Met Glu Lys Phe Asp Ser Met Glu Asn Ser Asp Val
        115                 120                 125
Asp His Lys Arg Lys Met Glu Phe Glu Phe Val Ser Ile Ile Asp Gly
130                 135                 140
Lys Glu Thr Val Ala Lys Ala Ala Asn Leu Leu Asn Lys Lys Tyr Tyr
145                 150                 155                 160
Ser Asp Ala Asn Thr Glu Lys Pro Phe Phe Thr Glu Thr Tyr Leu Thr
                165                 170                 175
Glu Ala Leu Arg Ile Leu Gly Ala Asn Glu Pro Asp Pro Asp Leu Leu
            180                 185                 190
Leu Ile Tyr Gly Pro Thr Arg Cys His Leu Gly Phe Pro Ala Trp Arg
        195                 200                 205
Ile Arg Tyr Thr Glu Met Val His Met Gly Ser Leu Lys Asn Lys Lys
    210                 215                 220
Leu Gly Leu Ile Phe Lys Ala Ile Asn Lys Tyr Thr Lys Val Lys Gln
225                 230                 235                 240
Asn Tyr Gly Ser
```

<210> SEQ ID NO 6
<211> LENGTH: 735
<212> TYPE: DNA
<213> ORGANISM: Lactuca sativa

<400> SEQUENCE: 6

```
atggatctcg taggtggacc ccagaagatt ttacacaaaa tctcactgaa tgatcacatg     60
atacttctgt tgctgtggca cattcttcat ttaattgttc aagtcatata ctttgtttgg    120
gagaagatgc gtgcaattga aagctatctt atagcaaatg gaattgtcaa acatatgaa    180
gatctgaatt tagacagagt gaagtatctt ggaattgtgg tggatagtga tgaagctcgt    240
gaaacctcaa aagttattga acttttggag tggatttcag atattggtgt gaaaaaggtc    300
tgcctttatg acagagaagg agtgttgaag aagtccaagg aactgttcat ggagaaattt    360
gattctatgg agaattcaga aactaatcaa aaaggaaaa tggattttga atttgtttca    420
atcgttgatg gaaaagaaac agttgctaaa gcagcgaatc tgctatataa aagtattat    480
```

| | |
|---|---|
| tctgatccaa attcagaaaa accattctttt actgaaacct atttgaccga agcacttagg | 540 |
| atcctaggtt ctaatgagcc ggatcctgat cttatactga tttatgggcc cacaaggtgc | 600 |
| caccttggtt ttccagcatg gcgtattcgt tatacagaga tggtacacat gggatcattg | 660 |
| aagaacaaga agtttggttt gattttgaaa gccatcaaca aatacaccaa ggtgaagcag | 720 |
| aactacggtt cttaa | 735 |

<210> SEQ ID NO 7
<211> LENGTH: 735
<212> TYPE: DNA
<213> ORGANISM: Taraxacum brevicorniculatum

<400> SEQUENCE: 7

| | |
|---|---|
| atggatctgt tagacggacc ccagaagatt tatcgcaaaa tctcacagaa tgagaacatc | 60 |
| gtgctattgt tgctgtggca tgttcttcat ttaattatca aatttatgta ctttgttcgc | 120 |
| gagatcttac gtggaattga aaactatctt ataataaatg aaattgtgaa acatatgaa | 180 |
| gatctgaatt taaacagagt gaaatatctt ggaattgtgg tggacagtga tgaagcacgt | 240 |
| gaaacttcaa aagttattga acttttggag tggctttcag atattggtgt gaaaaaagtg | 300 |
| tgcctttatg accgtgaagg agtgttgaag aaatccaagg aagtgttcat ggagaaattt | 360 |
| gattctatgg agaattcgga tgttgatcat aaaaggaaaa tggaatttga atttgtttca | 420 |
| attattgatg gaaagaaac agttgctaaa gctgcaaacc ttctaaacaa aaatattat | 480 |
| tcagatgcaa atacagaaaa accgttctttt actgaaacct acttgaccga ggcactcagg | 540 |
| atcttaggtg ctaatgagcc agatcctgat cttttactga tctatgggcc cacaaggtgc | 600 |
| caccttggat ttccagcatg gcgaattcgt tatacagaga tggtacacat gggatcactg | 660 |
| aagaacaaga aattaggttt gattttcaaa gccattaaca aatacactaa ggtgaagcag | 720 |
| aactacggtt cataa | 735 |

<210> SEQ ID NO 8
<211> LENGTH: 1599
<212> TYPE: DNA
<213> ORGANISM: Potato

<400> SEQUENCE: 8

| | |
|---|---|
| caagctactt acctcttata taaaaaagaa aaagtgtttc taatatatac tcaatttaaa | 60 |
| taaaatatttt tcaatcaaat ttagataaca aatacttatc aatatgaggt caataacaat | 120 |
| aaaaaaataa tgtaaaaaaa aaggagcaat acataatata agaaaaaaga ttaaagtgcg | 180 |
| attatcaacg agtattatac cctaatttgc taatatttaa actcttatat ttaaggttat | 240 |
| gttcacaata tacttaaaaa gcgctatatt agagcatata ttaattaata aaaagaaaa | 300 |
| tgctaaatga tcaaaaaaat tagatagaaa attaagaaaa ttataatatt tttttatttt | 360 |
| aaaataaatt gatatattct ttattttttta gttaaaatgt attaaagtta aagaataaa | 420 |
| aatatttttaa aaaataaaat aacataaata aaatatcatt ctaattaaat tcagaccaaa | 480 |
| ttttttcccc agattttggc caatacctaa aataaaatta agttattttt agtatatttt | 540 |
| tttacattga cctacatttt tctagttttt tctaaaggag cgtgtaagcg tcaacctcat | 600 |
| tctcctaatt ttccccacca cataaataaa agaaacggt agcttttgcg tgttgttttg | 660 |
| ctacactaca cctcattatt acacgtgtca tcatataatt ggctaaccct atgaggcggt | 720 |
| ttcgtctaga gtcggccatg ccatctataa aaggaacctt tctgcacctc attttttcat | 780 |
| cttctatctg acttctatta taatttctct caattgcctt taaatttctc tttcaaggtt | 840 |

-continued

```
agaaatcttc tctatttttt ggttttttgtc tgtttagatt ctcgaattag ctaagcaggt      900
gctgttaaag ccctaaaatt tgagtttttt ttccgttgtt ttgatgaaaa agcccctaat      960
ttgagttttt ttccgtcgat ttgatgccaa aggtttaaaa ttagagtttt ttcgtcggtt     1020
tgattctaaa ggcccaaaat gtggggtttt ccgggtgatt tgatgataat gccctagaat     1080
ttgagttttt ttatggtggt tgatgaaaa aggtcttgaa tttgatttt ttttccggt       1140 tgatttgatg aaaaagccct agaatttgtg attttcgtc ggtttgattc taaagcccta     1200
aaatttgagg ttttccggtt gttttgatga aaaagcccta aaatttgagt ttttccccg     1260 tgttttagat tgtttggttt taattctcga atcagttaat cagggagtgt gaaaagccct     1320
ataatttgag ttttttttcgt tgttccgatt gttgttttta tgactttgca gatgcagatc     1380
tttgtgaaaa ctctcaccgg aaagaccatc accctagagg tggaacgttc tgatacaatc     1440
gacaacgtta aggctgagat tcaggataag gaaggaattc ccccggatca gcaaaggctt     1500
atcttcgccg gaaagcagtt ggaggacgga cgtactctag ctgattacaa catccagaag     1560
gagtctaccc tccatttggt tctccgtcta cgtggtggt                           1599
```

<210> SEQ ID NO 9
<211> LENGTH: 3093
<212> TYPE: DNA
<213> ORGANISM: Potato

<400> SEQUENCE: 9

```
ccactagtaa cggccgccag tgtgctggaa ttcggcttgc ttggtcttac ttcatcgtcg       60 agaaagaaa gaagacttct atctacaagt ttaactcaaa cgtagttctt ttatttttt       120 gggtgtgaag tagtgtcaaa ccaaaatacc ctttctaaac aactattgtt tgtgaatata      180
ggttgtgttg tttctcattc ggaagaccaa gtcccacacc ctaaacttca ctgatgagaa      240
caacctccgc actctgggct gtttaatccc cggttgaaat catccaacca aactctcttt      300
atttcgagat tgaaaaggtc gatcaattat gatcaaagat aatgcctagt ggcgacgagc      360
ccactaggaa gacctttgat tacaaaggtt accgtggtct aggtttataa tggattcaat      420
taatcaaagt gcctccaact caatcaaagc tcattttcct atcaggagaa acaatgcat       480 aaaaaaggga tggccgtcaa aaagccgacc cttcaatcca aaagcgttca aattcccgcc      540
tacatcagct cgacctgttt gttcgctcta attaggatca tcagaatatc ttgacagatt      600
tttttgaaaa gcttaacttg caagcggaga atgccgagtc tctacccact ttttgagctt      660
gcaaagtagc aatatgaaat tcttgggca cttacccgtc gtgcttgaga tctaaactgc      720
ttacaacaac cttgacctgg tccaatgaaa agagaaagac ttaaagagct ccctctatag     780
gtgactcctc caataagact cttagggtgc atgtcaaaac ccgctaagtt aggagtatac     840
ataaaatttt ggccgatata aggattaata taaccaaata atataacgaa ataaattta      900 aacaataaaa aataataaag agatgtatcc attcttttc actcaaattg tattttaga     960 aattatagtc aaatttacta tcaaaattta aaaaattaat ttttaaaatt atacatgcca    1020
tgaatttgaa atttgaaaaa gggaaaaaga ggagaagcat ctagtaaggc tctaattaat    1080
tgcgtaaccg tgtcttctaa aatatccgaa gaaattgcgt aagcgctgag ccataggccc    1140
atacgttccc tctctgtgac ggcaaagcgg ttactataaa tacagatctt cccttttttca    1200 accaaatccc caaatcatca tccttctcta gcgcaacttc tctcggaaaa agcatctcc    1260 tcctcctctc gttttctcga taatctcctt gtacactgtt tcttcttctc aaggtaatgg    1320
```

```
tcttttcttc tctcgattca atcgtttgtt gaagtgattt agatttatgc aggttttttgt    1380 attataaatg tatgaacaga attatatgaa cggaatttac ctttgtttct tgtttatcga    1440
tcagatctgc acggaattag tcgatttgag aactttttga aatcgatgat gtatgttttt    1500
tctgttgatg atgctatagc gtttaatttc gtttgatttg ctcttgtttt ggtttccata    1560
tggtcgaatt gttgaagttt cgtagtttga ttagttttgt atcctatcta gggttttttg    1620
tgatcacaat taatcaattt gaaatggtga tgcttgcttt ttctgttgat gatgttatag    1680
cattgaattt cgttgatttg cttgattttt tggtcactgt ttaatagaaa ttgttcaagt    1740
ttccaggttt gattaattgt gtcctgtgta gggatattta tgatcaaaat taatcaattt    1800
gaagaaaaca ctatgtttaa tggataatat atgcttttt attttcttg ttgatgatgt    1860 tatagtcttg tatattctcg tgttgttcca tttttctgtt ttctatttgc ttgaaattgt    1920
tcaagtttct aggtttgatt atttgtgtgc tatctaggga ttttgtgat caaaattaca    1980 aatctaggtt aaatggatga tgcatgcttt tgctgctgat gatttatagc cttgaatttt    2040
gtcgatttgc ttcattttg gtctctattt aatgaaattg ttgaagtttc taggtttgat    2100
taattgtgtc ttgtctaggg ttttgcgaa caaattgaac tagatttaaa taaatttagg    2160
agtcctcaat tttttgttt gttaactctt attgatctgt ttttttaatg tatttattct    2220
tgtgtgggca cattgttatt ctcttctgat tatgctagat cgtgaacttg atttgattta    2280
caatacatcc aattgtgggt ttgcatccct ctaaaatgat aagtatagtt tgttctaggt    2340
agaattggat gcttctaggg gcctactgat ttgtttgtaa aaatggttgt tcattggatt    2400 gaattttat taaagaaaaa atctgaaatt ctaataattc ttgtaaatta ggttgatgtc    2460
agatctattt atttcttct ttgtttggtt gactggtctt ctggtggctc tctgattagt    2520
gtaattatag ttgactttgg atatgttgct tttgctcttt gtatggtttc taatcaattg    2580
ggattctttt cttattctct cctaatttgc ctctggtttg atatattcaa ttttaacttc    2640
aattgtttcg tgggatgact tgtcccaaat taaacaagtt ctgagatttg tgtgcaagct    2700
atgctatggg tgttcatatt atgtggtagt tcgctgctgt aagagggaga ttgcagaacc    2760
tttattatat cgtcttttct ttttggactt ccaaagcttg ctagtttgtc atctctgcct    2820
gattgaatag aattttgac agttgtgtgc ttgaatatat ttcagatgca gatctttgtt    2880
aagacactca ccggaaagac catcactctt gaggtcgaga gttctgacac cattgataat    2940
gtcaaagcta agattcaaga caaggaaggc attcctccag atcagcagag gctgatcttt    3000
gctgggaaac aacttgaaga tggccgaaca cttgctgatt acaacatcca aaaagagtct    3060
accctccatc ttgtccttcg tctacgtggt gga                                  3093
```

<210> SEQ ID NO 10
<211> LENGTH: 1173
<212> TYPE: DNA
<213> ORGANISM: Arabidopsis thaliana

<400> SEQUENCE: 10

```
taagttctgt aaaaaaggtt tacctttcta ctttgccgga aaactcaact cacggtggcg      60
tccggcgagt tttcagacca aaagaaggt tggaagaaat gaagatgaag aggagaggac    120
aaaagataga gatggtggtt gaacaaaaga agagtaaaga ggacgaagac gctctaagtc    180
taagccaagg gggagaagaa gagaagaggt atgaggagga accatacttt tgttagagag    240
atgctggaaa ttgtgatcaa ctacatgcaa atgtctttt cgcctaacca cttaccatat    300
ttgatatttt cctttttgcca aattacacaa accctatctt gtctctcaca tatatatcca    360
```

```
attaatacac ccctgccact tgttaattct cgaccatgta tgtatactta tgtaaagaat      420
atccaaaagc tttctttttg ttccttcgat tttaagcaac ttgtgttctc atttctcaat      480
atcttaaaga aatcctgagt aaaagtttat agcctccgtg aatcttagga aattactcta      540
gcatattcaa attttttgag acaatatata aattttctg aataattaaa tttacatatc       600
tatgctacga aacttgatta attaaatcaa atatatatat atatataata ataataataa      660
taatataaca tttttttag dacacaaata tctaatctca ctatactcta gaagtatttg       720
caatgcacga tatgtgaatg gagaaaagac agaaagagca tttgaaaata tctcgtttca      780
cggatcatta tgtctaatta ttttaccata gaaaagcgac aattataaac aatttgttat      840
tcgtggaaaa ataatattta ataatggttg tcgtacccta taaactacag ccacacattc      900
atacaataag aagttaaaaa aattcatacc ctaaaggcat caaccagtga agggtcagaa      960
acttcccaag atgggtcaaa ggacacatgt cagattctca gtgattgaca gccttgataa     1020
ttacaaaacc gtgggatcgc ttagctgttt cttatccacg tggcattcac agagacagaa     1080
actccgcgtt cgaccccaca aatatccaaa tatcttccgg ccaatataaa cagcaagctc     1140
tcactccaac atttctataa cttcaaacac tta                                  1173

<210> SEQ ID NO 11
<211> LENGTH: 2129
<212> TYPE: DNA
<213> ORGANISM: Hevea brasiliensis

<400> SEQUENCE: 11
aataatgtaa tgaagagtag aacactagta ttttttttt ttttttggtt attttgttgt        60
atgttatatt tgaatctatt caaaatttgg atggacaaaa tgaataattg tggtgagtgt      120
gataggatat aggataaaat ggatgagcat gaaaagtgtg atgagcaatc ttaaaatacc      180
tgatataatg aaaaataatt tatacaaaac tgtgatcaaa ttagctattt ctatttatct      240
atttataatc cctctcctac tgtagcaacc attaatgcct ttataatccc tcccctagtt      300
ccatgctctt attgttttcc atctatttat tacagatctt cctgggtcct agaatcagac      360
cttaaggatg agttctggct gcatggatct ttgggtcatg acttggacaa gtttgctcca      420
aattttaacc tttggcggtc cgcccccac tggggctagg aaggctaatc ttaaccttt       480 cctaagagat gtcattatcc aatttccagg gccattgctc aatttgagag gagaaccact      540
tgcaaaagta ataaatactg tcaccaccct tcaatacaga taaccaaact gaattttaaa      600
ttaactaaat ttttaattga tttttgatttt attaattgat caaaattgaa aatatttaat      660
caaatattat tattaattaa aaaaattaca aattaaatat tattcataaa attataaaag      720
taataattat aaataatata ttattaaaaa taataattaat ataaattcaa ttattctaat     780
taattcaata ataaatcaa agataattga attgataatc aaaaattaaa gtaaacaaaa       840 ttcatttta ttaaaataat taaatttcat tggttcaatt cagttatcac tgaataatgc        900
attccactca cttacatctg tgtagtcaag ttcctcattg cttctatttc atgctcctca      960 tcccttcgt tggacttaca atttggagca aacacaaaac tcaagcttat ttattaatgg     1020
aaaatagttt tttgttttt ttttgtttaa agaatatttt tatttttatt ttttataaa       1080 aataaaaaat attaaaaaat acgttcactt gttagcaata aagaacaatt ttttagttaa     1140
aaaaatgttt caaaatcgt tcatatcttt aataatttaa aaaatagaac attataaaag      1200
acatttaaaa gctcagttat tattaaaatt ttttaaatat acgtcgttta tttactttat     1260
```

| | |
|---|---|
| aataatatga ttaaaaattt tatgaataca attaaatatt tttctaaata attattaatt | 1320 |
| gtatttatga aagttatagt ataattttaa ttatataaaa aatattattt tttaaataaa | 1380 |
| aactatttga caagagaact tttgttgtaa aggaaaaaca atggattatc acttaaagta | 1440 |
| attttctaaa ttttagttca attttgaaaa acttgaaagc atggcacatt taaatatgaa | 1500 |
| aatcctcatt gtaattttat gggaaaattt tttcagaaaa ctactctaat tttcataagt | 1560 |
| aaacatactc tagagcttcc attttttaaga aggtttaaaa aaaattttct tttgtttttc | 1620 |
| aaaaataact tatgtatata atctgtatac gtcatatgta ataagtttct taaaaaacat | 1680 |
| ttcaggaatg aaagatttag aaaggttatt ttaacgttca aatctattaa atgattaatg | 1740 |
| actgttccaa aaatttatat ttattgtgga aatcatcctc aaaaaaaaaa aaaatccaat | 1800 |
| atgataaaag atttgaattt ttaagcggtt atttaatttt gaaaacaag gctaactttt | 1860 |
| tttttttatat aatttactaa aaaattcatg aatgaaaaaa aaaatccata agtaaactta | 1920 |
| ccccatacgg gttatgcacg ctaaaccaat aaaacagaaa cacgtttata cactcgtttt | 1980 |
| cattttccat ctataaatag agagatttgt ttttagtttt aaaccataat cagttgatag | 2040 |
| cttccacagt gttttccgaa aggcaaatct ttttcaaac ttcagcgact gcgttttgaa | 2100 |
| tttgtgattt ttaaaggaaa ttttcaatt | 2129 |

<210> SEQ ID NO 12
<211> LENGTH: 3199
<212> TYPE: DNA
<213> ORGANISM: Hevea brasiliensis

<400> SEQUENCE: 12

| | |
|---|---|
| aaactcagaa aaatttgtag actccaaata tattttagt tttgccacgt ggtctttaaa | 60 |
| taaattttt tttaaaatca tcaaagtttt atattttcgg gaaatcaaac ccgatttaa | 120 |
| aaatccgaaa aatttaaat aatttcctaa aatttaaata aataaaata ttaatattac | 180 |
| tctcaaaata ataaatttaa aaatttgggt tgttacatta ttagtgagta ttttcatcgg | 240 |
| cgattgtctt ttcccttct ctttttgatt ttttcatatt tattttgtgt ttttcttaaa | 300 |
| aatctccaaa tttgtatcat tttggaatag atctttgttt gttctcaatc atttgagttt | 360 |
| tatttcctcc tttgagagta tttgttgtct actcttttat gagtatttgg tattcctcc | 420 |
| ttttcaagaa tttattattt ccttcattac gaggatctgt tctttttttt ttcttttctt | 480 |
| ttcatcatgg agatgttagg aatgttgctt tattatttgg gtagaagtat aatgatagta | 540 |
| agtaaatatt ttctcttctt gacatatcaa aatttgatta ttttcaaatc aatctgctag | 600 |
| agagattgtg gagttaaaca gtgatagatt atcactaagt ggggtgtgct tcctattaaa | 660 |
| aggtcaactc aattaatttg tcaatacgat taagtctttt aagtaaagat aattgttatt | 720 |
| atattttgta taaataattt atcttatatt ttttatgca aaattatagt attgtgaaat | 780 |
| tttatactcc atatatgcat tcttttctcaa tttattaaaa actctatttt ttatttttta | 840 |
| aaaataatat tgaatctttt tctaaaatta taaaatgttt aaacaataaa attttattag | 900 |
| tttaataaat tcgattcatt ttatgctttt tttaaaattt tgaagttta atttaataac | 960 |
| tgaattatta attattgata tactaatttt aattctatta ataatatatc ttttataata | 1020 |
| acattttata attatttta ttaaaagtat atcatatttta ttattttta aaataaaata | 1080 |
| taattataga tatatttttt tcaatatttt actgattagc aatgtaaatt atatattata | 1140 |
| attttttatt ataatcgtta accaacgact aaatattgat tatatttatt tttttgtca | 1200 |
| aacttaattt aatgattatt tttaaattat taaaaattca gcattcattg aggctatgaa | 1260 |

```
ttcatcacca cctttcattt cttatattgg actatttggg aaaatcattt ttttaaatat    1320
attaatttta aaaataatt taattaaat ttaataaatt ttatttataa aaatattaaa    1380
ataataaaat aatattttt gatttctttt aacaatatta aaaataatat ttttatttta    1440
aaaaataatt ttagctctct aatctcgatg ctcaacaaat accatatctc ttagtcaatt    1500
gccttattgc ttcccacctc atggttctta accgttggat tcaaaagtat gtgttggagc    1560
aaacacaaaa ctacaggcct cccaggtttt ttaaaaaaa aaaaaaactt ttctacgcat    1620
aaattttcca agaaaaatat ttttgaggaa taatttattt ttattattct gttaaaatct    1680
gaaaataaag aaaaattact tcctaatggt tcaaggaaaa aataacaatt ttattttgt    1740 ttataatatt atgaaaatat ttaaattata aactttaat ttttattttt ttattgtgaa    1800
atgtataaaa aatacataaa ataataaat tgtgttttag ccatcctggc tgttgaggcc    1860
gcaaggcccg caagcagtag ccggtaaagg aaaaaccagg ggcaatattt ttgcagggtt    1920
tttttttttt ttttttttt tttcttaaa agtaaagaac gtatgtatga gtcttaaaga    1980
tagtaatttt aatagagtct ttgatcttat ataattctca cacatttta caatctgatg    2040 tggaatccta aagtactaac tcgtgtctat gcccaccact cgcaaacttc aatcaggatc    2100
acatcatgga ctctcatttt ttctttattt tcacttaagt gattattttt ttttttttt    2160 atcaaagata aagaatatac acacatatta gaaacatgat tagataatta taaaaaaagg    2220
ataattttaa tgaaattttt aattctatat aattcattca cacatacttt catcgcttaa    2280
tatgagatat gaaggaattt agccttagtt tggttaagaa ttaatataaa ttaaaattat    2340
attgtattag attaaattaa aataaaaata ttaaattaat ttttttagaa aaattaaaat    2400
tgatcttgaa ccaaactcaa ataaagttaa tttgatccct tcattttttt ttatttaat    2460 gaaaatttaa attgagatct tgtaattttg gaagccattt aaatattatc gatttgctaa    2520
taattatgct gaatgtaatt taatggtaaa gaaaataaat aataaaaaag atacatttaa    2580
tttaatttaa tttatatatt ttttttatttc aaaaaatttt aaaaaggaac agattgttaa    2640
atctttattt tttcaattaa attaaattaa ttgagtctca aatataatat tttataatct    2700
taaaaataat tttaatatta ctgatttaaa tttatagatt taatttaaaa attttttaaaa    2760 gtaaagaaaa taattaagat tttaattttt aagtcgcacg tgattttgaa tttaatttt    2820 taaaaacaaa gactaactta tttttttata atttattaag aaaatcatga aaatccccat    2880
tctaaatcga cttctggaac cgggatgatg cgtttgcttt gcgatactcc atgtgcttta    2940
cttaccccat aaggatcatg cgcgaatcac gatagaacca atacaacagc aacacgttta    3000
cacgctcctt tcttaacag ctggcctgcc attcacga atttccatct ataagtagag    3060
aggtttggtt ttagcatcaa accataatcg gttgatagcc tccatcagcg ttttcagaaa    3120
ggcgggtttc ttttttgaaa cttaagcgac tgcgttttga attttgatct tccattttg    3180 caaaaggaaa tcttcgatt                                                3199

<210> SEQ ID NO 13
<211> LENGTH: 2294
<212> TYPE: DNA
<213> ORGANISM: Hevea brasiliensis

<400> SEQUENCE: 13
taagatgcta acgtgcttct tttattagct taaccttttc gattattaga tataaaattt      60
aaaaaaaaaa agaaaaataa ttttagaaag caaaacgtaa ttataactaa taatttcttt     120
```

```
cgacgagaaa gtattgttta tttaaatatc tttatccttg tttattttt  aaattgattc   180 tgctaaatta tcttttatt  ttatgtatct ccattgatta acagcatata aatattcact   240
tattgtacac aaagtcgatt aatagaaaac ttacatacat ccaagccaat agctctcagg   300
ccaaagaaat taaccaacc  caagagcgag caacaaacca acacaaaaag gccacaggaa   360
ctgaaaccat aagttggcca tgaaacaaaa agtaaatcaa taaatcagca cctggaactt   420
ccttcctagg actaacaaaa accaggacaa aatagaataa cctgcaactc catagtcaat   480
tttgatgcct caagccacat cttcttgttg tagttgtttt tggagtgttt gaaacgtatt   540
tcattttcgt aaaacaagtt ttgtattaga atgcatattt ttctgcatta aaatgcaaaa   600
gtttaaaaga gaaacaaaaa ccttgcattt gaaggccaac aaaattgttt ttggtgtgtt   660
tcaaacttca ttttagata  acaaactttg cagcaaaata tcattttttg tgcattagaa   720
tgcgaaaatt aaaagagaa  acaaaaatac caacagtaaa catttgcaca gagagagaac   780
catccattca aactcaattt gcatcttttt ttggttgctt tcaagtagca cccactgaca   840
gtagattcca aagctagctc ttgtgaaaga gacttaatct taactgttgg tttatgtaat   900
ataaaaatct atttagaaaa gctttcaaga cacatgttta caatttcccc acatcatctt   960
ctcttctctt tattcttgtg gtccattaag atttctcatt cgagtgctca agttgcaaac  1020
cacttttgat tttggaggat ttaccgagtc acctacaggc ttcgggtaat agcgaataaa  1080
cctttaagga cagtaacatc atggtttgct gtaaattagt tccctccctt gctcttcatt  1140 tccctttct  tttagtatcc tagtttgttc taagatttcg gtattgcata atttatactt  1200
ggtaatgttt agaattgctt atcccaata  acttcttcat aacaaattta aaataaaatt  1260 attttttgc  ttataaaaaa aatttaaat  aaaaccatga aatattcaaa ttttttttag  1320
ctaaattaga aatctaccgt gcattaacat acttaatttg ttgatataaa tacatctttg  1380
accaaagtct ttttattttt tttgtttgat tgtgttcaaa tttaagacct tataattta   1440 aaaactactc taatactact gaattaattc ttattatcaa agtcctcctc tttataaat   1500 taaaaataa  taataaatta attttaaaat aacttttag  tagtcttttt tgaattaaaa  1560
aaaataatat atatataaat atatatatat atatatatat atatatatat atatatatat  1620
atatatatat atattattgg aactatgatt ttttttttt  ctgatgaaca ggttaaagca  1680
ttgtgatgtg ggtttaagga aatggaatta tacaccagta agaggcaaag tgtgtctaca  1740 cttttgga   agcttatgag aaaagggtta tatggcattt ttttaacccg gggtctcatc  1800
cttataaaaa aaaaatttaa atcaaaacca ttctttgtgc gtataataaa aaaaataaaa  1860
taaaaccatg acatattcaa tttccttaac taggttaaaa atttttcatg cataagcata  1920
ttcttaattt gttgataaat agactttaga tcaactctca acatgaccaa attctctcct  1980 ttttttaat  ataattggtt tcaattgaaa ttcaaactct agattgtata atttatgaac  2040
gatttcaata ccactaagct aatactcaaa ggtcaaagta ctcacaatag catcaagtag  2100
tctttttaag gttaaagaaa cttttatata tatatatata tatatatata tatatatata  2160
tatatattta tatttatata ccacttgatt tagtatcact tccaaaataa tcaacttaat  2220
ttagttattg gaactgagat ttttttttt  ttccgtttt  ctgatgaaca ggttaagtca  2280
gtggtttaag gaaa                                                    2294
```

<210> SEQ ID NO 14
<211> LENGTH: 29
<212> TYPE: DNA
<213> ORGANISM: Artificial Sequence

```
<220> FEATURE:
<223> OTHER INFORMATION: Chemically Synthesized

<400> SEQUENCE: 14
tcaagatacc actctactat ggatctagt                                              29

<210> SEQ ID NO 15
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 15
attttgctcc ccttgagtc                                                         19

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 16
atggaagtca atccaatcat c                                                      21

<210> SEQ ID NO 17
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 17
gaagaagaag caggcttga                                                         19

<210> SEQ ID NO 18
<211> LENGTH: 2133
<212> TYPE: DNA
<213> ORGANISM: Parthenium argentatum

<400> SEQUENCE: 18
aggccaaaaa aactcaatcc ggaggcccaa taacaccccg ccgtaagcta tggcccacaa            60
accgttgctt acggtttgtg ccttctgatc tcttttacct tttgcaatct gtaagctacg           120
atctataaac tgtagcttac tgttgacagc ttattcctaa aactattttc ttcataactt           180
tttcgtttca actccgtttt ccttgatttt cacgaccacg ttttcgtttt tcaaccctct           240
attatggcat gtactaatac cttcatttcc acttcatgta tgttttccaa aacacataca           300
atcttcgtgt ttaacctaca aaacctcaat ttccttgtag tattcaattc cagtattcca           360
cacatatcaa cacacaaaaa cgcataagat tcaacattta agcacttaaa tactcatgcc           420
agacccttgc catcaataac caactagtac tttacccgtc cggtgacgga acatcagcgt           480
cgtgatatca acactaaacg tggtggggg aatgcgttca atccgccgac atcaaacatc            540
accgaatcaa aatcaaatat caccgcataa aaagcggaga gaagatccaa atacattcta           600
aaagctccga ttgagtttat atggctgaga tttgatattg gtggagttta aacggctcaa           660
atcgattcat ggagcggtta cactataccg catccatata atatataatt tatcggtaaa           720
ttaaaggacc ataccataaa tcgtcggtta atattggtta tcagttaatt cggttcggtg           780
atggtttgat taactagtta atttcggtta acggttaagg tttgctcacc cctaccccta           840
```

```
cttagaacta tttagaaatt atgaatacta tattataatt tcatttctta ttgttatatg    900
caataaaaat gcttcagtta tataaagtgc tatctatata ctatagaatt ttatcatttc    960
gattatacaa cccgtataat acacaggtct ataacacaat tattatatat aatactaaaa   1020
atgccacact ttaatgtgtg gcatcgctaa cgtgcaccgc ctctaaagcg catcgcctgc   1080
taacatacac cagccatatt tagtgttgca tttctaacgt gcgctgcccg ctaatgtgca   1140
ccgaccatat tttgctaaag tacaccgata tttacttatt tatttttta aggttaagca   1200 ttgttttttc tttcttttg gggatacgca tttggtacca ggtatttgta caaaaccagt   1260
attttcagta tcggtatagt gatattttc tttatcgtgg agaactgaac cggtactgtt   1320
ttaatacagg taccaatacc gtattcatat ttgtattttc tcaacgtgaa agtataatat   1380
tatccctaat gccatcaaa tcctcaacga tataaacgtc acccgaaaca agaacgaag    1440 aacatactaa cactatatag aaaagtaaaa aaaatccaaa gtttaacatg ccgacacctc   1500
aaaagtcaca accatgatga acataccgaa gtaacttcta tccggcggca cgaccgtccg   1560
gtttcatctc taattaaact aggacaacaa ccatcgccga cgttggtttt cgggcgaact   1620
ttacatttaa cggtgggttt agttctcatt ggcaatactt gggggggggg ggggggcatg   1680
gtggctcagt aaagaaggtt gagatctcta tgattttcag ttcaattctg agggcgtccg   1740
gtttttacca ccagtggccc ttcggacggt tggattttcc ctggaacagg agataaacttt  1800 gtgcacttaa gggctccgta tgactaggtt ggaccaacta gctgtgatct tttaccattt   1860
ggtcactccc tacaaactta acaattcaat aattacttgc cgttaaaaaa aaaatctcac   1920
tgtatgagtg gaaggtttag ggggttgtag gtaaggtaga ggcgtgtatt aacctactct   1980
cttatattat acacgtggca gtctcttcta acacacatga ttagcgtttc ccacactttt   2040 gttattttc tcgtagatcc aaccaaatat aaattataca cctccgttaa tggttgtaga   2100
gcttccataa ttaacctcca cacttctctt atc                                2133
```

<210> SEQ ID NO 19
<211> LENGTH: 19
<212> TYPE: DNA
<213> ORGANISM: Parthenium argentatum

<400> SEQUENCE: 19

```
ggcggtcatc atggagaga                                                  19
```

<210> SEQ ID NO 20
<211> LENGTH: 24
<212> TYPE: DNA
<213> ORGANISM: Parthenium argentatum

<400> SEQUENCE: 20

```
gattggctac tgcactatca ttgg                                            24
```

<210> SEQ ID NO 21
<211> LENGTH: 20
<212> TYPE: DNA
<213> ORGANISM: Parthenium argentatum

<400> SEQUENCE: 21

```
ttgaatgcca ggctttggtt                                                 20
```

```
<210> SEQ ID NO 22
<211> LENGTH: 18
<212> TYPE: DNA
<213> ORGANISM: Parthenium argentatum

<400> SEQUENCE: 22
gcgcgcatga ccttctca                                                   18
```